US012558189B2

(12) United States Patent
Rebellino et al.

(10) Patent No.: US 12,558,189 B2
(45) Date of Patent: Feb. 24, 2026

(54) METHODS AND APPARATUS FOR DIRECT MARKING

(71) Applicant: Devicor Medical Products, Inc., Cincinnati, OH (US)

(72) Inventors: Jordan Rebellino, Cincinnati, OH (US); Justin Rebellino, Cincinnati, OH (US); Nathan K. Busick, Lebanon, OH (US); David C. McBreen, Cincinnati, OH (US); Garrett A. Householder, Cincinnati, OH (US); Andrew Small, Cincinnati, OH (US); Jessica P. Leimbach, Cincinnati, OH (US); Andrew P. Nock, Dayton, OH (US); Kinito Swader, Monroe, OH (US); Bryan Superville, Elmont, NY (US); Natasha M. Guerrero, Liberty Township, OH (US); Michael J. Sunderman, Cincinnati, OH (US); Raj Thapar, Cincinnati, OH (US); Gary Wagner, Independence, KY (US)

(73) Assignee: Devicor Medical Products, Inc., Cincinnati, OH (US)

( * ) Notice: Subject to any disclaimer, the term of this patent is extended or adjusted under 35 U.S.C. 154(b) by 940 days.

(21) Appl. No.: 17/527,398

(22) Filed: Nov. 16, 2021

(65) Prior Publication Data

US 2022/0071732 A1 Mar. 10, 2022

Related U.S. Application Data

(63) Continuation of application No. PCT/US2020/035184, filed on May 29, 2020.
(Continued)

(51) Int. Cl.
| | | |
|---|---|---|
| A61B 90/00 | (2016.01) | |
| A61B 10/02 | (2006.01) | |
| A61B 17/34 | (2006.01) | |

(52) U.S. Cl.
CPC .......... *A61B 90/39* (2016.02); *A61B 10/0233* (2013.01); *A61B 17/3468* (2013.01);
(Continued)

(58) Field of Classification Search
CPC ................ A61B 90/39; A61B 17/3468; A61B 2090/3987; A61B 2090/3991
See application file for complete search history.

(56) References Cited

U.S. PATENT DOCUMENTS

| | | | |
|---|---|---|---|
| 3,620,216 A | 11/1971 | Szymanski | |
| 4,936,835 A | 6/1990 | Haaga | |
| | (Continued) | | |

FOREIGN PATENT DOCUMENTS

| | | | |
|---|---|---|---|
| JP | 2002-508227 A | 3/2002 | |
| JP | 2002-537891 A | 11/2002 | |
| | (Continued) | | |

OTHER PUBLICATIONS

Extended European Search Report dated Nov. 23, 2023 for Application No. 23202702.9, 4 pages.
(Continued)

*Primary Examiner* — Jason M Sims
*Assistant Examiner* — Ari Singh Kane Padda
(74) *Attorney, Agent, or Firm* — FBT Gibbons LLP

(57) ABSTRACT

A marker delivery device includes a grip, a cannula, a push rod, and a marker element. The cannula extends distally from the grip. The push rod is configured to move within the cannula and includes a distal end with one or more seals configured to seal against an interior of the cannula. The marker element includes one or more barbs. The push rod is
(Continued)

configured to generate a pressure within the cannula between the one or more seals and the marker element to eject the marker element from the cannula.

15 Claims, 29 Drawing Sheets

Related U.S. Application Data

(60) Provisional application No. 62/854,356, filed on May 30, 2019.

(52) U.S. Cl.
CPC ................. *A61B 2017/3454* (2013.01); *A61B 2090/3908* (2016.02); *A61B 2090/3987* (2016.02); *A61B 2090/3991* (2016.02)

(56) References Cited

U.S. PATENT DOCUMENTS

| | | | |
|---|---|---|---|
| 6,083,524 A | 7/2000 | Sawhney et al. | |
| 6,162,241 A | 12/2000 | Coury et al. | |
| 6,181,960 B1 | 1/2001 | Jensen et al. | |
| 6,270,464 B1 | 8/2001 | Fulton, III et al. | |
| 6,356,782 B1 | 3/2002 | Sirimanne et al. | |
| 6,572,626 B1 | 6/2003 | Knodel et al. | |
| 6,605,294 B2 | 8/2003 | Sawhney | |
| 6,994,712 B1 * | 2/2006 | Fisher .................... | A61B 90/39 |
| | | | 606/116 |
| 7,465,279 B2 | 12/2008 | Beckman et al. | |
| 7,736,330 B2 | 6/2010 | Bardy | |
| 8,221,358 B2 | 7/2012 | McKay | |
| 8,600,481 B2 | 12/2013 | Sirimanne et al. | |
| 8,939,910 B2 | 1/2015 | Fisher | |
| 2005/0228311 A1 * | 10/2005 | Beckman ............... | A61B 90/39 |
| | | | 600/564 |
| 2012/0226146 A1 * | 9/2012 | Schwartz ............... | A61B 90/98 |
| | | | 359/871 |
| 2013/0066195 A1 * | 3/2013 | Sirimanne ........... | A61K 49/222 |
| | | | 600/424 |
| 2014/0371586 A1 * | 12/2014 | Ryan ................. | A61M 37/0069 |
| | | | 600/431 |
| 2017/0231716 A1 * | 8/2017 | Ahari .................... | A61B 10/02 |
| | | | 600/431 |
| 2019/0125401 A1 * | 5/2019 | Chacon Quiros .. | A61B 17/3468 |

FOREIGN PATENT DOCUMENTS

| | | |
|---|---|---|
| JP | 2005-288175 A | 10/2005 |
| JP | 2007-526065 A | 9/2007 |
| WO | 2015/077421 A1 | 5/2015 |

OTHER PUBLICATIONS

Japanese Office Action dated Apr. 2, 2024 for Application No. 2021-569925, 18 pages.
International Search Report and Written Opinion dated Oct. 7, 2020 for Application No. PCT/US2020/035184, 15 pages.

* cited by examiner

METHODS AND APPARATUS FOR DIRECT MARKING

PRIORITY

This application is a continuation of International Application Number PCT/US2020/035184 entitled "Methods and Apparatus for Direct Marking," filed on May 29, 2020, which claims priority to U.S. Provisional Application Ser. No. 62/854,356 entitled "Method and Apparatus for Direct Marking," filed on May 30, 2019, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of markers used after breast biopsies to mark the location where the biopsied tissue was removed is described in the following US Patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US Patents are incorporated by reference in their entirety.

Once a marker is placed at a biopsy site, the marker can later be relocated to identify the biopsy site in subsequent follow-up procedures. In some contexts, a placed marker may not completely correspond to the biopsy site. For instance, the marker may migrate from the biopsy site to another nearby location during the intervening time between the biopsy procedure and subsequent follow-up procedures. In addition, or in the alternative, the marker may not have been placed at the biopsy site during marking. In either case, this could lead to difficulties with identifying the biopsy site during subsequent follow-up procedures. Accordingly, it may be desirable to incorporate features into a marker to maintain the maker in a fixed position over time. In addition, or in the alternative, it may be desirable to incorporate features into a maker delivery device to increase marker placement accuracy.

While several systems and methods have been made and used for obtaining a biopsy sample and marking a biopsy site, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIGS. 1A, 1, and 1C show exemplary aspects of placement of a biopsy site marker, in accordance with aspects of the present disclosure;

Figures 1A, 1B, 1C:
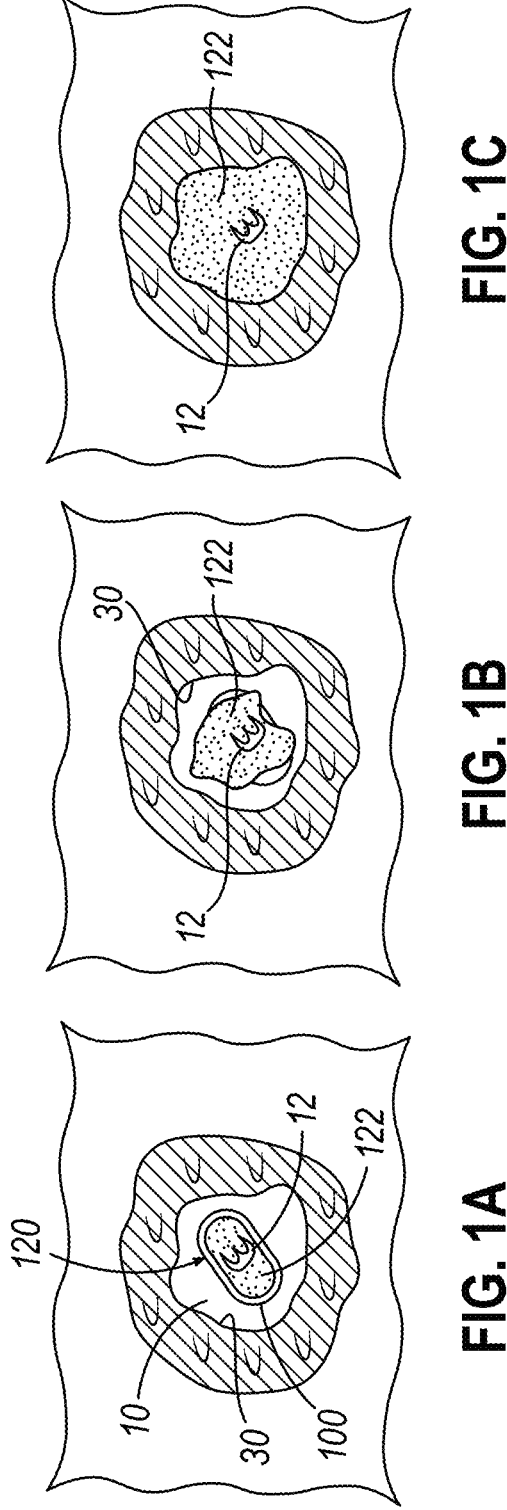

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples, marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured, and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel-based marker material (122) centers marker (100) in the biopsy cavity as it grows. As the hydrogel expands, naturally present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

Figure 2:
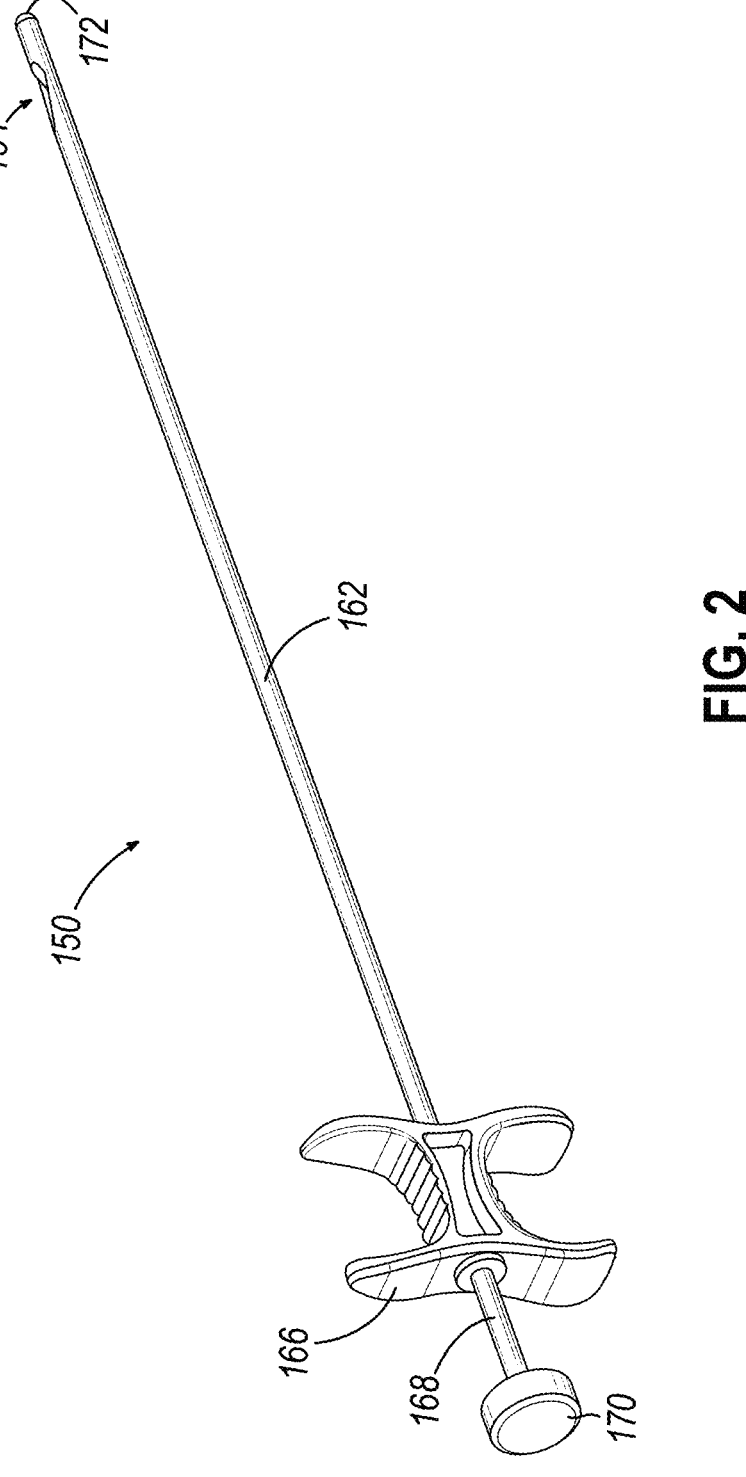
FIG. 2 depicts a perspective view of an exemplary marker delivery device.

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164); yet be relatively flexible in bending. A plunger (170) is coupled at the proximal end of rod (168) for forcing rod (168) distally in cannula (162) to deploy a marker out of cannula (162).

A user may grasp grip (166) with two fingers; and may push on plunger (170) using the thumb on the same hand, so that marker delivery device (160) is operated by a user's single hand. A spring (not shown) or other feature may be provided about rod (168) to bias rod (168) proximally relative to grip (166) and cannula (162).

Figure 3:
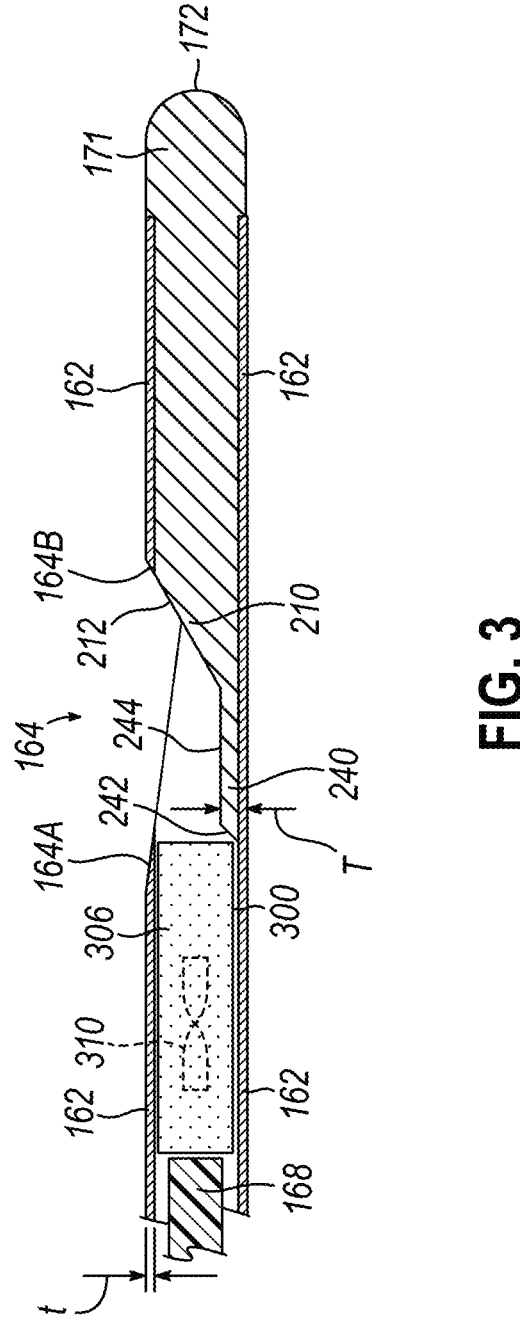
FIG. 3 depicts a side cross-sectional view of the marker delivery device of FIG. 2.

FIG. 3 shows a cross-sectional view of a distal portion of the marker delivery device (160). As can be seen, a biopsy marker (300) similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212); and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (22) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
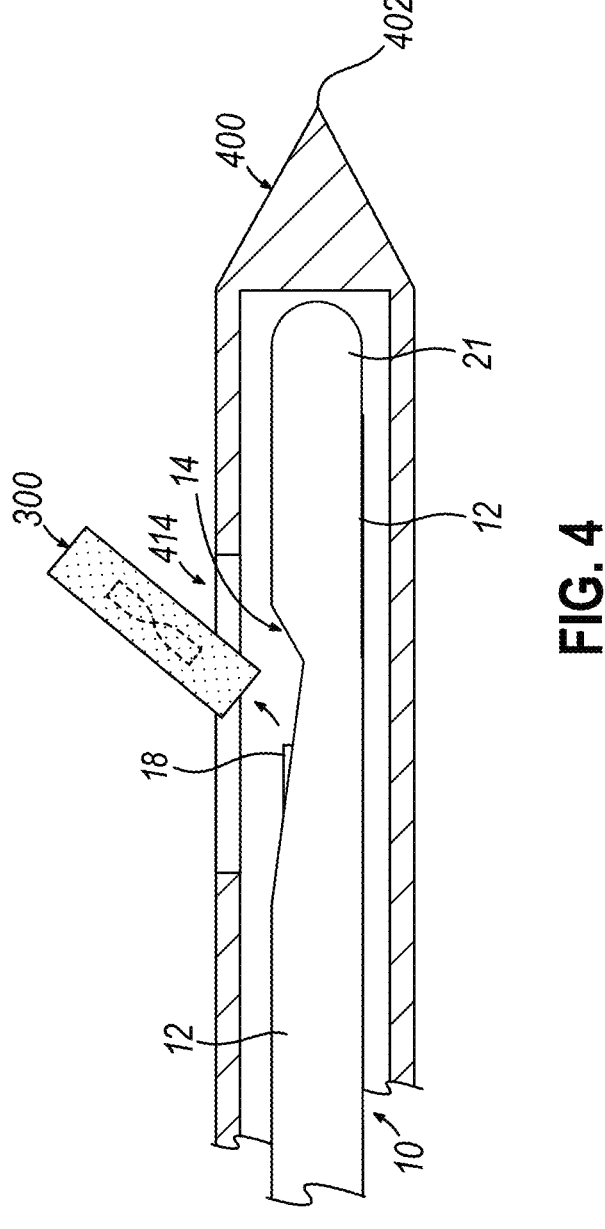
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (160) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (160) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 4 shows the distal end of marker delivery device (160) disposed within needle (400). Needle (400) may be positioned in tissue, and a biopsy sample may be obtained through lateral aperture (414), thereby providing a biopsy cavity adjacent lateral aperture (414). Then, after the tissue sample has been obtained and transferred proximally through needle (400), and without removing needle (400) from the patient's tissue, marker delivery device (160) is inserted into a proximal opening in needle (400). In FIG. 4, needle (400) and marker delivery device (160) are positioned such that opening (164) of cannula (162) and lateral aperture (414) of needle (400) are substantially aligned axially and circumferentially. Then, with marker delivery device (160) and needle (400) so positioned at the biopsy site, push rod (168) is advanced to deploy marker (300) up ramp surface (212), through opening (164), and then through lateral aperture (414), into the biopsy cavity.

III. Exemplary Alternative Markers and Marker Delivery Devices for Direct Marking In some examples it may be desirable to include various features associated with a marker similar to marker (100) to increase the propensity of the marker to remain in a predetermined position within tissue. In particular, once a marker is placed at a biopsy site, the marker can later be relocated to identify the biopsy site in subsequent follow-up procedures. In some examples, a placed marker may not completely correspond to the biopsy site. For instance, the marker may migrate from the biopsy site to another nearby location during the intervening time between the biopsy procedure and subsequent follow-up procedures. This could lead to difficulties with identifying the biopsy site during subsequent follow-up procedures. Accordingly, it may be desirable to incorporate features into a marker to maintain the maker in a fixed position over time.

In addition, in the alternative, in some examples it may be desirable include various features associated with a marker delivery device similar to marker delivery device (150) described above to increase accuracy of the initial deployment of the marker. In particular, as noted above, markers can be used to relocate a biopsy site. Also as noted above, in some examples, a placed marker may not completely correspond to the biopsy site. For instance, the marker may not have been placed at the biopsy site during marking. Thus, it may be desirable to incorporate features into a maker delivery device to increase marker placement accuracy. Although several examples are described herein that incorporate the features outlined above, it should be understood that various alternative combinations can be used without departing from the basic principles described herein.

A. Exemplary Marker with Dart

Figures 5, 6:
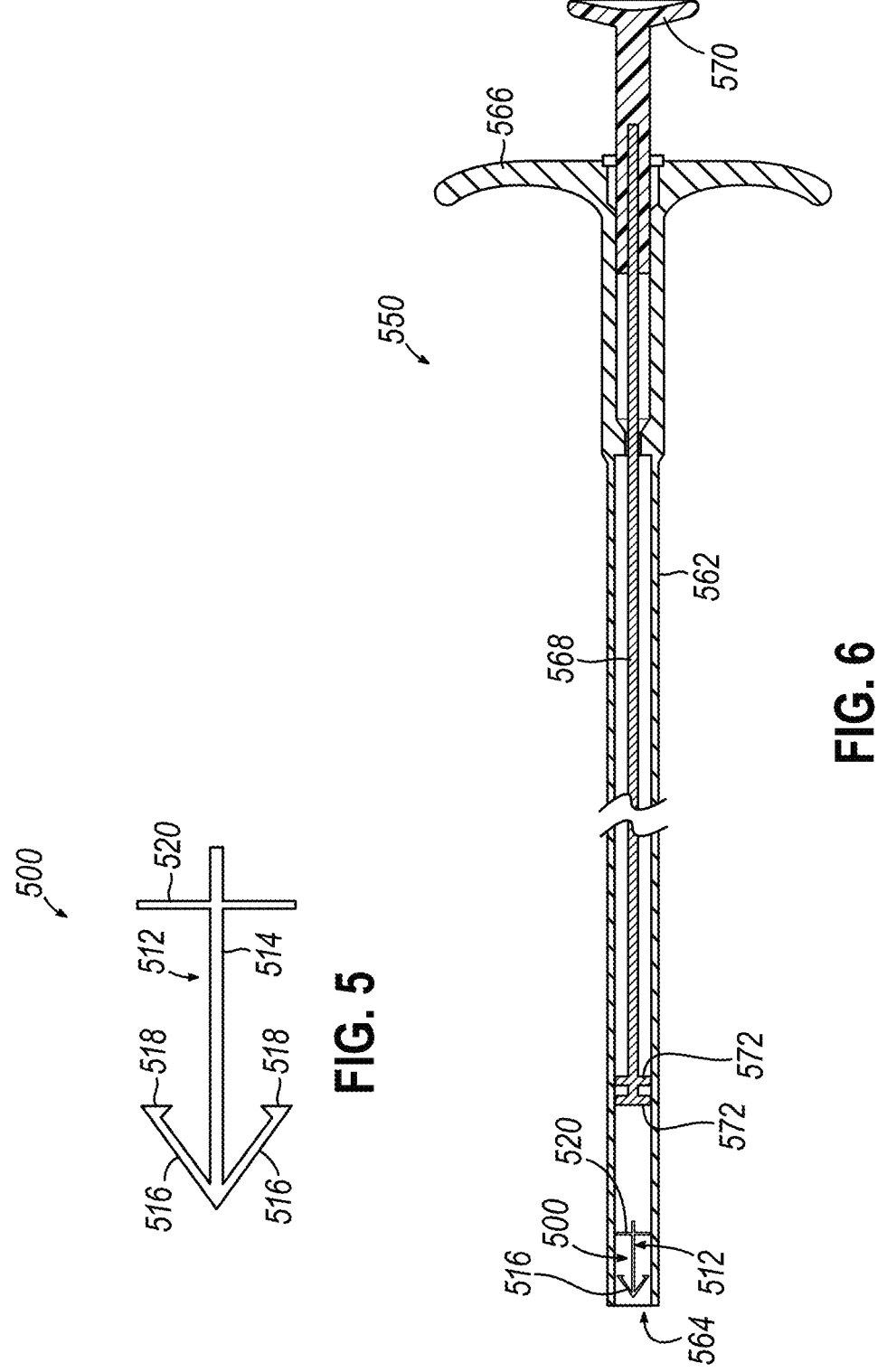
FIG. 5 depicts a side elevational view of another exemplary biopsy site marker.
FIG. 6 depicts a side cross-sectional view of another exemplary marker delivery device, the marker delivery device in a loaded configuration.

FIG. 5 shows an exemplary marker (500) similar to marker (100) described above. Marker (500) is generally configured to include an arrow or dart configuration that is generally configured to bite into tissue such that marker (500) resists movement once placed in the tissue. Unlike marker (100) described above, marker (500) of the present example is configured as a bare marker such that no carrier similar to carrier (120) is used. Although marker (500) of the present example is configured without a carrier, it should be understood that in other examples some or all of marker (500) can include a coating or other substance similar to carrier (120) described above.

Marker (500) of the present example includes a marker element (512) comprised of a material that is generally visible under a variety of imaging means such as x-ray, ultrasound, Magnetic Resonance Imaging (MRI), visual, and/or etc. Marker element (512) defines a geometry generally configured to bite into tissue. In particular, marker element (512) includes one or more arms (516) extending proximally and outwardly relative to a body (514) at an angle. In the present example, two arms (516) join at body (514) to define a configuration corresponding to the shape of an arrow or triangle. Thus, arms (516) together define a pointed distal end that can be used to penetrate tissue. In other configurations, only one arm (516) can be used. In other examples, multiple arms (516) can be used such as three, four, or five. Of course, various other configurations will be apparent to those of ordinary skill in the art in view of the teachings herein.

Each arm (516) includes one or more teeth or ribs (518) a proximal end of each arm (516). Such teeth (518) extend laterally inwardly relative to the outward extension of each arm (518). In this configuration, teeth (518) are configured to partially pierce or grab onto tissue segments to thereby hold marker (500) in a fixed position once placed within tissue. Although teeth (518) can comprise a variety of configurations, teeth (518) of the present example are configured as barbs with sharp ends.

A proximal portion of marker element (512) includes a base (520) extending outwardly from body (514). In some examples, base (520) can be configured to improve the trajectory of marker (500) during deployment by generally improving the balance of marker (500). Base (520) can also be configured to help with manipulation of marker (500) or also increase the propensity of marker (500) to remain in position once placed within tissue. Although base (520) of the present example is shown as having two outwardly extending protrusions, it should be understood that base (520) can have a variety of configurations. For instance, although not shown, base (520) of the present example can include a circular disk configuration. As will be described in greater detail below, examples of base (520) including a disk configuration can be used to seal various components such as the interior of a marker delivery device.

B. Exemplary Marker Delivery Device with Pressure Induced Deployment

FIG. 6 shows an exemplary marker delivery device (550) that can be readily used with marker (500) or any other marker described herein. Marker delivery device (550) of the present example is substantially similar to marker delivery device (150) described above except as otherwise noted herein. For instance, like marker delivery device (150), marker delivery device (550) of the present example includes an elongate outer cannula (562). Marker delivery device (550) likewise includes a grip (566) at the proximal end of cannula (562). Similarly, a push rod (568) similar to push rod (168) can be provided. Like with push rod (168), push rod (568) extends coaxially within cannula (562) such that push rod (568) is configured to translate within cannula (562) to displace one or more markers. A plunger (570) is coupled at the proximal end of rod (568) for forcing rod (568) distally in cannula (562) to deploy a marker out of cannula (562).

Unlike marker delivery device (150), marker delivery device (550) of the present example is generally configured as an end-deploy device rather than a side-deploy device. In particular, outer cannula (562) defines an open distal end (564) that is used as a marker exit in lieu of a side opening similar to side opening (164). Such a configuration can be desirable in contexts were marking occurs through an introducer with an open distal end rather than a needle similar to biopsy needle (400). For instance, in such configurations the open distal end of the introducer can be positioned with close proximity to a biopsy site and a marker can be deployed through the open distal end of the introducer. This configuration can generally be desirable to make marking simpler and to reduce the potential for error.

Although not shown, it should be understood that, in some examples, outer cannula (562) can include certain features configured to hold a marker within outer cannula (562). For instance, in some examples, outer cannula (562) can include an inward taper at open distal end (564). In other examples, outer cannula (562) can include one or more bumps, dimples, ridges, ribs, and/or etc. In such examples, suitable bumps, dimples, ridges, and/or ribs can be elastomeric or rubberized to permit a marker to pass through open distal end (564), while also holding the marker therein. In still other examples, various alternative configurations will be apparent to those of ordinary skill in the art in view of the teachings herein.

Marker delivery device (550) also differs from marker delivery device (150) in the configuration of push rod (568). In particular, the distal end of push rod (568) of the present example includes one or more disk-shaped seals (572) protruding outwardly from the core of push rod (568). Each seal (572) is sized to have a diameter approximately equivalent to the inner diameter of outer cannula (562). In addition, seals (572) can include a sealing portion such as a rubberized coating or o-rings to seal against the inner diameter of outer cannula (562). In this configuration, seals (572) are configured to generally provide a sealed fit within outer cannula (562) to seal at least a portion of outer cannula (562). As will be described in greater detail below, this configuration can be used to generally build pressure between a marker and push rod (568) to thereby eject the marker using pressure rather than physical contract between push rod (568) and the marker.

Figure 7:
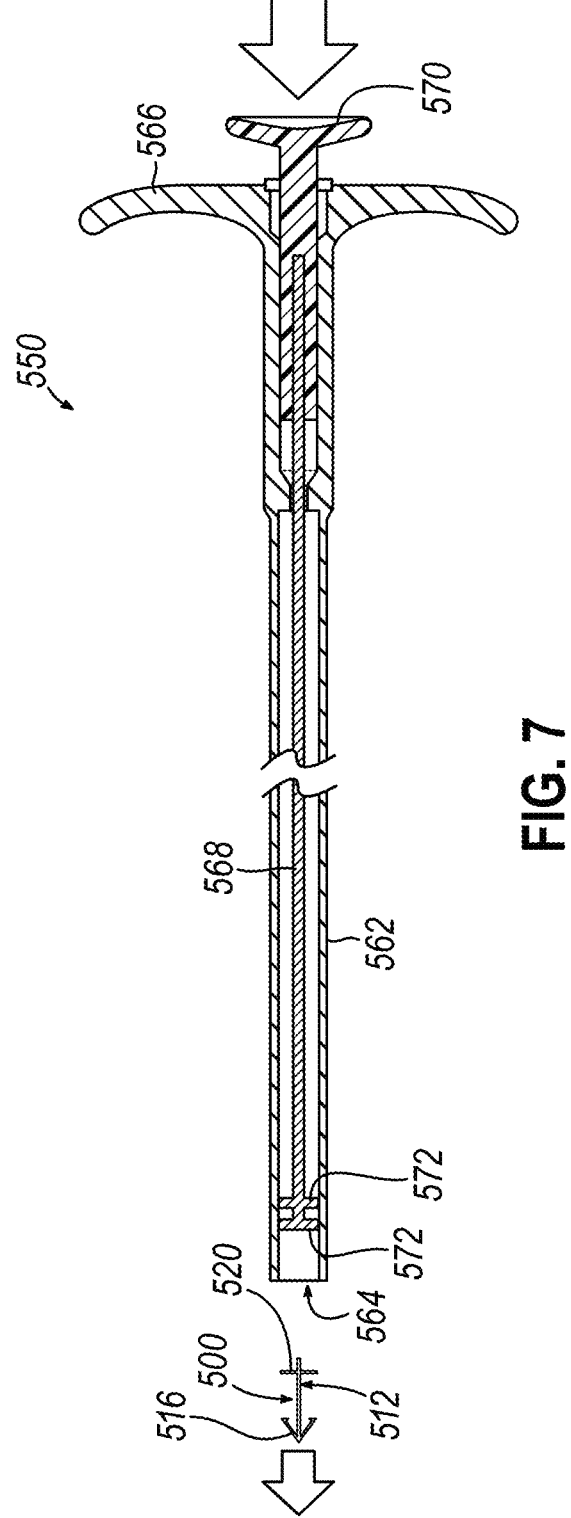
FIG. 7 depicts another side cross-sectional view of the marker delivery device of FIG. 6, with the marker delivery device in a deployed configuration.

FIGS. 6 and 7 show an exemplary use of marker delivery device (550) in connection with marker (500). Although marker delivery device (550) of the present example is shown as being used with marker (500), it should be understood that in other examples marker delivery device (550) can be readily used with any other suitable marker including but not limited to markers described herein.

As seen in FIG. 6, marker delivery device (550) initially begins in a loaded configuration. In the loaded configuration, marker (500) is disposed within outer cannula (562) of marker delivery device (550), just inside open distal end (564). In addition, at least a portion of maker (500), such as base (520), can engage the interior of outer cannula (562) to seal against outer cannula (562). Push rod (568) is positioned proximally of marker (500) to define at least some space between marker (500) and push rod (568). As will be described in greater detail below, this space generally defines a volume within the interior of outer cannula (562) that can be used to generate positive fluid pressure between marker (500) and the distal end of push rod (568).

While marker delivery device (550) is in the loaded configuration, outer cannula (562) marker delivery device (550) can be inserted into tissue of a patient to position open distal end (564) at a biopsy site. In some uses, introduction of marker delivery device (550) can be with performed without the aid of an introducer cannula, biopsy needle, or other associated device. In other uses, introduction of marker delivery device (550) can be performed through a biopsy needle similar to biopsy needle (400) described above. In still other uses, introduction of marker delivery device (550) can be performed with the aid of an introducer cannula used in connection with a biopsy needle or other associated device. In all uses, positioning of open distal end (564) can be confirmed using one or more forms of imaging guidance such as x-ray, ultrasound, MRI, and/or etc.

Once outer cannula (562) of marker delivery device (550) is positioned within tissue, marker (500) can be deployed through open distal end (564) as shown in FIG. 7. To deploy marker (500), an operator can push plunger (570) to translate push rod (568) distally. In some uses, this can be accomplished using a single hand with the aid of grip (566). As push rod (568) is advanced distally, one or more seals (572) on the distal end of push rod (568) cause positive fluid pressure to build between marker (500) and push rod (568). In the present example, base (520) of marker (500) assists in building positive fluid pressure by providing at least some sealing action proximate open distal end (564). This pressure continues to build until marker (500) is ejected from open distal end (564) and into tissue.

Once marker (500) is deployed from marker delivery device (550), outer cannula (562) can be withdrawn from the tissue. At this stage, one or more additional markers similar to marker (500) can be optionally deployed either with marker delivery device (550) (after reloading) or other marker delivery devices similar to marker delivery device (550).

C. Exemplary Marker with Releasable Tether

Figures 8, 9:
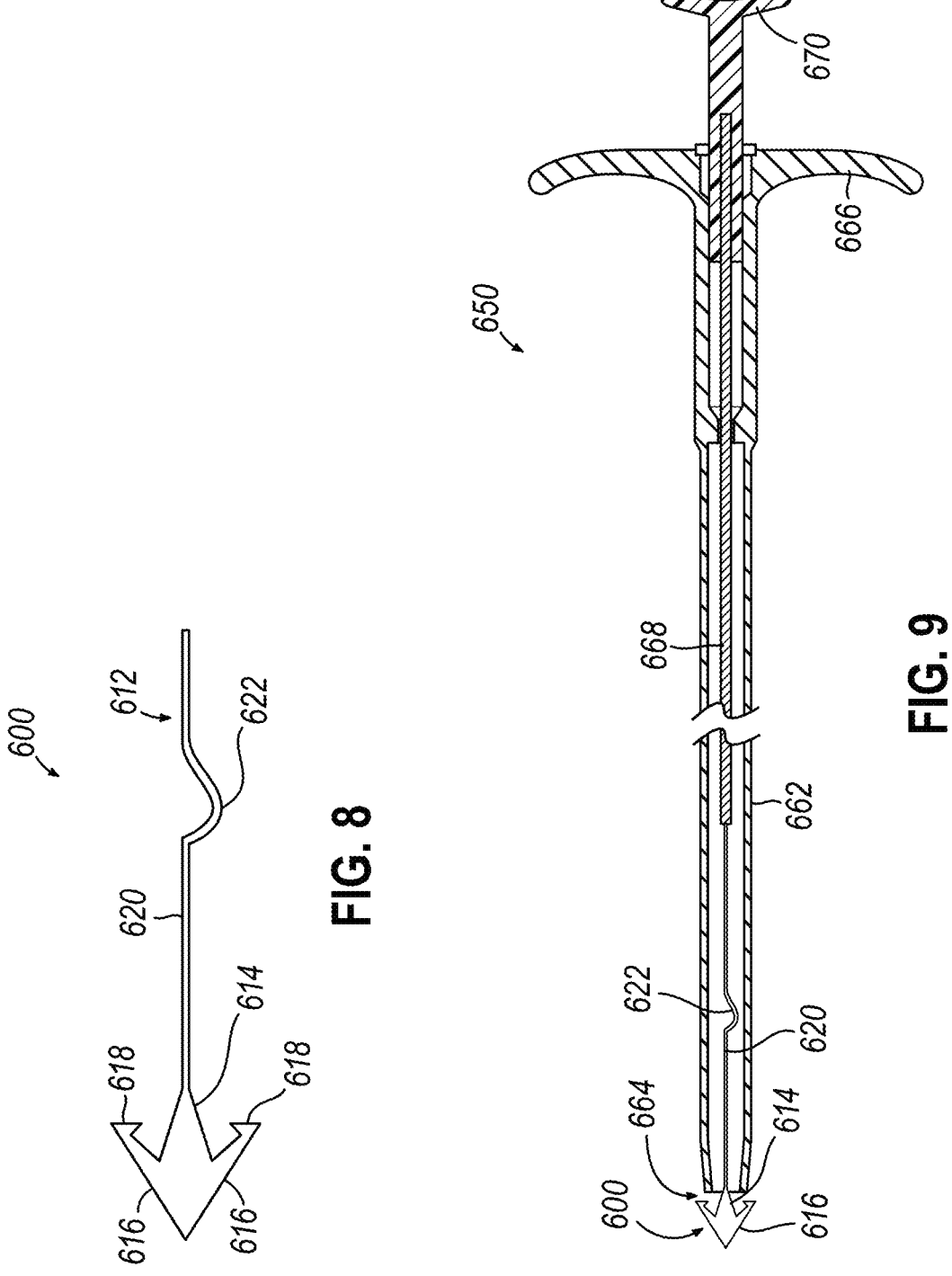
FIG. 8 depicts a side elevational view of yet another exemplary biopsy site marker.
FIG. 9 depicts a side cross-sectional view of yet another exemplary marker delivery device, the marker delivery device in a loaded configuration.

FIG. 8 shows an exemplary marker (600) similar to marker (100) described above. Marker (600) is generally configured to include an arrow or dart configuration that is generally configured to bite into tissue such that marker (600) resists movement once placed in the tissue. Unlike marker (100) described above, marker (600) of the present example is configured as a bare marker such that no carrier similar to carrier (120) is used. Although marker (600) of the present example is configured without a carrier, it should be understood that in other examples some or all of marker (600) can include a coating or other substance similar to carrier (120) described above.

Marker (600) of the present example includes a marker element (612) comprised of a material that is generally visible under a variety of imaging means such as x-ray, ultrasound, MRI, visual, and/or etc. Marker element (612) defines a geometry generally configured to bite into tissue. In particular, marker element (612) includes one or more arms (616) extending proximally from a body (614) at an angle. In the present example, two arms (616) join at body (614) to define a configuration corresponding to the shape of an arrow or triangle. Thus, arms (616) together define a pointed distal end that can be used to penetrate tissue. In other configurations, only one arm (616) can be used. In other examples, multiple arms (616) can be used such as three, four, or five. Of course, various other configurations will be apparent to those of ordinary skill in the art in view of the teachings herein.

Each arm (616) includes one or more teeth or ribs (618) a proximal end of each arm (616). Such teeth (618) extend laterally inwardly relative to the outward extension of each arm (618). In this configuration, teeth (618) are configured to partially pierce or grab onto tissue segments to thereby hold marker (600) in a fixed position once placed within tissue. Although teeth (618) can comprise a variety of configurations, teeth (618) of the present example are configured as barbs with sharp ends.

Body (614) of marker element (612) projects proximally away from the distal end of maker element (612) and tapers inwardly as body (614) extends proximally. In some configurations, this tapering configuration can be configured to promote a seal between marker (600) and other elements such as a marker delivery device cannula.

The proximal end of body (614) is integrally coupled to a tether (620) that extends distally from body (614). As will be described in greater detail below, tether (620) can be used to couple marker (600) to a portion of a marker delivery device. In the present example, tether (620) is generally configured as a thin wire such that tether (620) can be flexible and non-rigid. Although tether (620) of the present example is generally flexible, it should be understood that in some examples tether (620) can be configured to have at least some rigidity and/or stiffness.

Tether (620) of the present example includes a crimp (622) near body (614). Crimp (622) is generally configured to act as a stress concentration point for tether (620) such that stress applied to tether (620) concentrates in crimp (622). As will be described in greater detail below, this stress concentration can generally be used to provide controlled breakage of tether (620) for use in deployment of maker (600). It should be understood that in other examples, crimp (622) can take on a variety of forms such as a perforation, a necked portion, or other features configured to promote the concentration of stress.

D. Exemplary Marker Delivery Device with Crimp Release

FIG. 9 shows an exemplary marker delivery device (650) that can be readily used with marker (600) or any other marker described herein. Marker delivery device (650) of the present example is substantially similar to marker delivery device (150) described above except as otherwise noted herein. For instance, like marker delivery device (150), marker delivery device (650) of the present example includes an elongate outer cannula (662). Marker delivery device (650) likewise includes a grip (666) at the proximal end of cannula (662). Similarly, a push rod (668) similar to push rod (168) can be provided. Like with push rod (168), push rod (668) extends coaxially within cannula (662) such that push rod (668) is configured to translate within cannula (662) to displace one or more markers. A plunger (670) is coupled at the proximal end of rod (668) for forcing rod (668) distally in cannula (662) to deploy a marker out of cannula (662).

Unlike marker delivery device (150), marker delivery device (650) of the present example is generally configured as an end-deploy device rather than a side-deploy device. In particular, outer cannula (662) defines an open distal end (664) that is used as a marker exit in lieu of a side opening similar to side opening (164). Such a configuration can be desirable in contexts were marking occurs through an introducer with an open distal end rather than a needle similar to biopsy needle (400). For instance, in such configurations the open distal end of the introducer can be positioned with close proximity to a biopsy site and a marker can be deployed through the open distal end of the introducer. This configuration can generally be desirable to make marking simpler and to reduce the potential for error.

It should be understood that, in some examples, outer cannula (662) can include certain features configured to hold a marker within outer cannula (662). For instance, in the present example outer cannula (662) includes an inward taper at open distal end (664). In other examples, outer cannula (662) can include one or more bumps, dimples, ridges, ribs, and/or etc. In such examples, suitable bumps, dimples, ridges, and/or ribs can be elastomeric or rubberized to permit a marker to pass through open distal end (664), while also holding the marker therein. In still other examples, various alternative configurations will be apparent to those of ordinary skill in the art in view of the teachings herein.

Marker delivery device (650) also differs from marker delivery device (150) in the configuration of push rod (668). In particular, the distal end of push rod (668) of the present example is fixedly secured to the proximal end of marker (600). As can be seen, tether (620) of marker (600) couples directly to the distal end of push rod (668). The coupling between tether (620) and push rod (668) can be by any suitable means such as mechanical fastening, magnetic fastening, adhesion bonding, welding, integral connection, and/or other suitable coupling means. As will be described in greater detail below, the coupling between tether (620) and push rod (668) is generally configured to hold tether (620) within outer cannula (662) until push rod (668) is actuated using plunger (670).

Figures 10, 11:
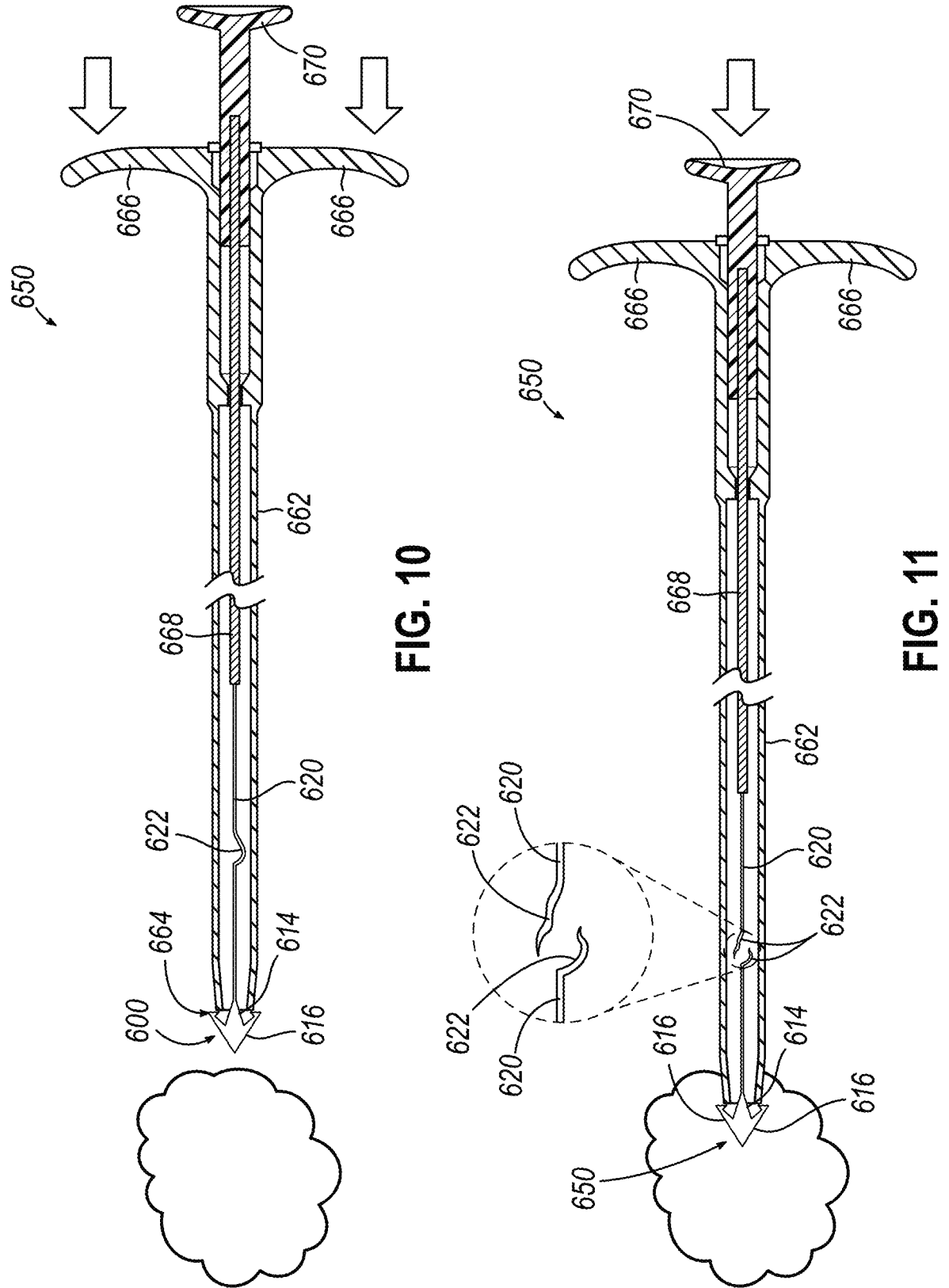
FIG. 10 depicts another side cross-sectional view of the marker delivery device of FIG. 9, with the marker delivery device being inserted into tissue.
FIG. 11 depicts yet another side cross-sectional view of the marker delivery device of FIG. 9, with the marker delivery device in a deployed configuration.

FIGS. 10 and 11 show an exemplary use of marker delivery device (650) in connection with marker (600). Although marker delivery device (650) of the present example is shown as being used with marker (600), it should be understood that in other examples marker delivery device (650) can be readily used with any other suitable marker including but not limited to markers described herein.

As seen in FIG. 10, marker delivery device (650) initially begins in a loaded configuration. In the loaded configuration, body (614) of marker (600) is disposed within outer cannula (662) of marker delivery device (650), with arms (616) resting on the distal end of outer cannula (662). In some examples, at least a portion of maker (600), such as arms (616), can also seal against a portion of outer cannula (662) to prevent ingress of fluid into outer cannula (662).

In the loaded configuration, push rod (668) is generally positioned in a relaxed position such that tension on tether (620) of marker (600) is relatively low. This tension generally holds marker (600) within outer cannula (662). At the same time, this tension is low enough so as to not deform or otherwise stretch or bend tether (620).

While marker delivery device (650) is in the loaded configuration, outer cannula (662) marker delivery device (650) can be inserted into tissue of a patient to position open distal end (664) at a biopsy site. In some uses, introduction of marker delivery device (650) can be with performed without the aid of an introducer cannula, biopsy needle, or other associated device. In other uses, introduction of marker delivery device (650) can be performed through a biopsy needle similar to biopsy needle (400) described above. In still other uses, introduction of marker delivery device (650) can be performed with the aid of an introducer cannula used in connection with a biopsy needle or other associated device. In all uses, positioning of open distal end (664) can be confirmed using one or more forms of imaging guidance such as x-ray, ultrasound, MRI, and/or etc.

Once outer cannula (662) of marker delivery device (650) is positioned within tissue, marker (600) can be deployed through open distal end (664) as shown in FIG. 11. To deploy marker (600), an operator can push plunger (670) to translate push rod (668) distally. In some uses, this can be accomplished using a single hand with the aid of grip (666). As push rod (668) is advanced distally, stress is applied to tether (620) of marker (600). This stress concentrates and builds in crimp (622) until crimp (622) breaks. After crimp (622) is broken, marker (600) is released from marker delivery device (650). Because arms (616) are already positioned on the outside of outer cannula (662), teeth (618) can secure marker (600) in place through engagement with tissue that occurred previously during placement. Outer cannula (662) of marker delivery device (650) can then be withdrawn from the tissue, leaving behind the portion of marker (600) distal of crimp (622).

Once marker delivery device (650) is withdrawn from the tissue, one or more additional markers similar to marker (600) can be optionally deployed either with marker delivery device (650) (after reloading) or other marker delivery devices similar to marker delivery device (650).

E. Exemplary Marker Delivery Device for Pre-Biopsy Marking

Figure 12:
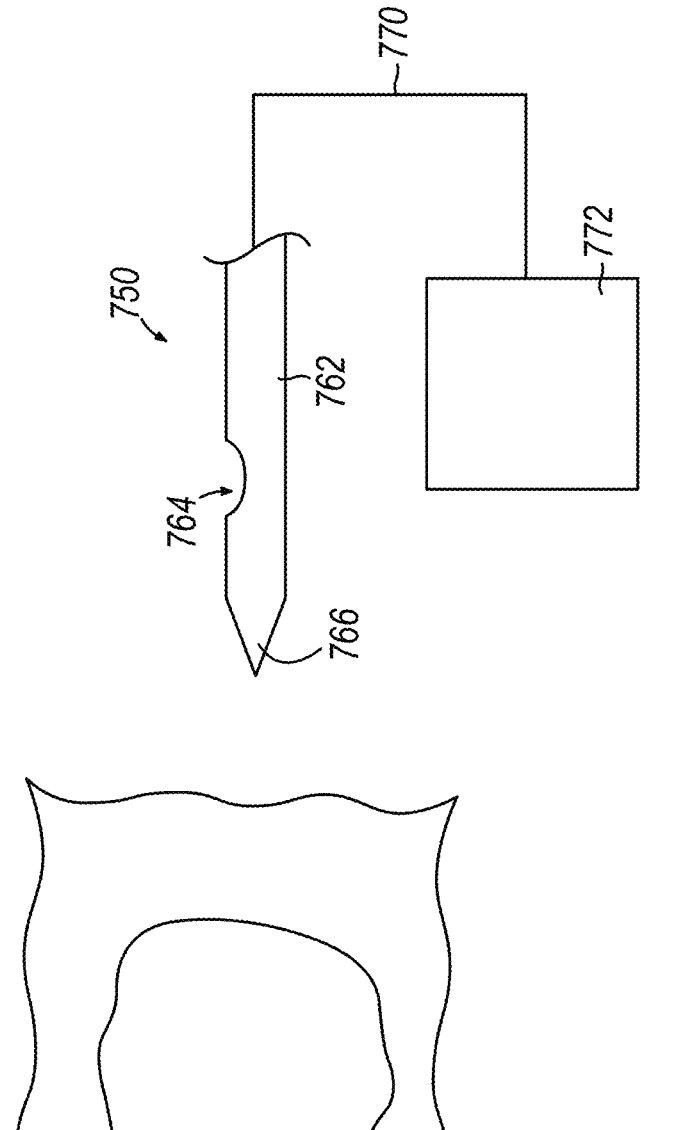
FIG. 12 depicts a side elevational view of still another exemplary marker delivery device.

FIG. 12 shows an exemplary marker delivery device (750) that is configured to mark tissue prior to removal of a biopsy sample. As will be described in greater detail below, marker delivery device (750) is generally configured to inject a fluid-based marking substance. However, it should be understood that in other examples marker delivery device (750) can be readily used with various solid markers described herein.

Marker delivery device (750) of the present example is substantially similar to marker delivery device (150) described above except as otherwise noted herein. For instance, like marker delivery device (150), marker delivery device (750) of the present example includes an elongate outer cannula (762). Although not show, it should be understood that marker delivery device (750) likewise include a grip similar to grip (166) at the proximal end of cannula (762). Also like with outer cannula (162) described above, outer cannula (762) of the present example includes a side opening (764) to act as a marker exit similar to side opening (164) described above.

Unlike marker delivery device (150), maker delivery device (750) includes a sharp tip (766) at the distal end of outer cannula (762). Sharp tip (766) is generally configured to pierce and penetrate tissue. As will be described in greater detail below, in some uses outer cannula (762) can be used as the first instrument to be inserted into tissue. Thus, sharp tip (766) is generally desirable to promote penetration of tissue without assistance from other devices such as a biopsy needle similar to biopsy needle (400), an introducer, stylet, and/or obturator. To promote such penetration, it should be understood that sharp tip (766) can have a variety of forms. For instance, in the present example, sharp tip (766) has a generally conical shape. In other examples, sharp tip (766) can be multi-faceted with a plurality of cutting edges. In yet other examples, sharp tip (766) can have one or more blades intersecting a conical core. Of course, sharp tip (766) can have a variety of other suitable configurations as will be apparent to those of ordinary skill in the art in view of the teachings herein.

Also unlike marker delivery device (150), marker delivery device (550) of the present example is configured to deploy a fluid-based marking substance. Accordingly, in the present example a structure similar to push rod (168) is omitted. Instead, the proximal end of outer cannula (762) is coupled to a fluid source (772) by way of a tube or catheter (770). Fluid source (772) is generally configured to supply a marking fluid to an inner lumen extending through outer cannula (762). Fluid source (772) can additionally be configured to provide such fluid under pressure. In the present example, fluid source (772) is shown schematically. However, it should be understood that fluid source (772) can take on a variety of forms such as a syringe, a motor driven pump and tank, a pressurized fluid tank, and/or a gravity fed fluid bag. Of course, in other examples fluid source (772) can have various alternative configurations as will be understood by those of ordinary skill in the art in view of the teachings herein.

FIGS. 12 through 15 show an exemplary use of marker delivery device (750) to mark a biopsy site prior to performing a biopsy procedure. As best seen in FIG. 12, marker delivery device (750) initially begins outside of tissue in a loaded configuration. In the loaded configuration, marking fluid is contained within fluid source (772) for later deployment at a targeted biopsy site. At this stage various preparations for insertion of outer cannula (762) into tissue can be made. For instance, the tissue can be scored to promote insertion. Alternatively, a targeting set or other device can be inserted into tissue to assist insertion of outer cannula (762).

Figure 13:
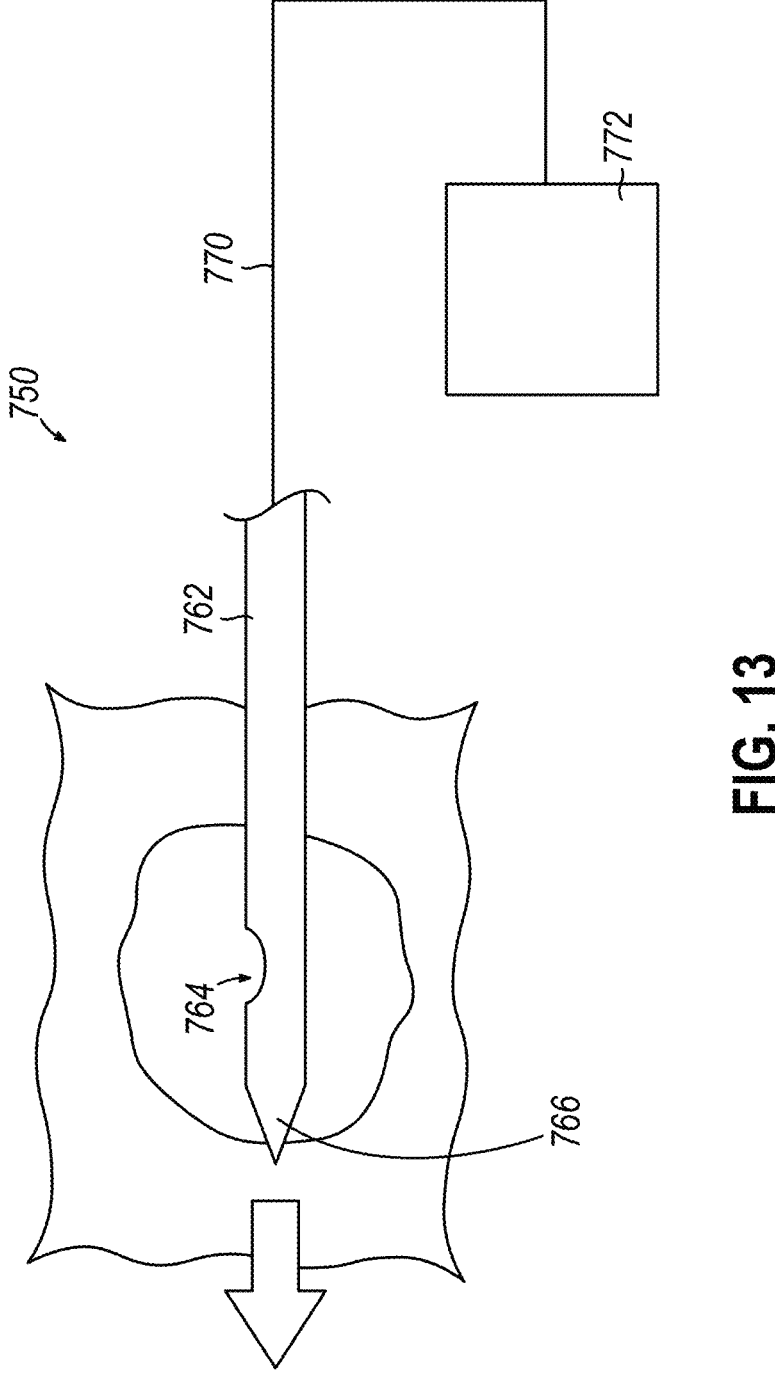
FIG. 13 depicts another side elevational view of the marker delivery device of FIG. 12, with the marker delivery device being inserted into tissue.

Regardless of how tissue is prepared, outer cannula (762) can be inserted into the tissue once the preparations are made. As seen in FIG. 13, outer cannula (762) can be inserted directly into tissue using structures similar to grip (166) described above. Alternatively, outer cannula (762) can be inserted into tissue using various assisting mechanisms such as a firing mechanism or an introducer cannula inserted into the tissue prior to insertion of outer cannula (762). In either case, outer cannula (762) is inserted into tissue to align side opening (764) with a lesion or other feature that is targeted for biopsy sampling. It should be understood that, in some examples, outer cannula (762) can be used with an imaging guidance means such as x-ray, ultrasound and/or MRI to provide proper alignment of side opening (764).

Figure 14:
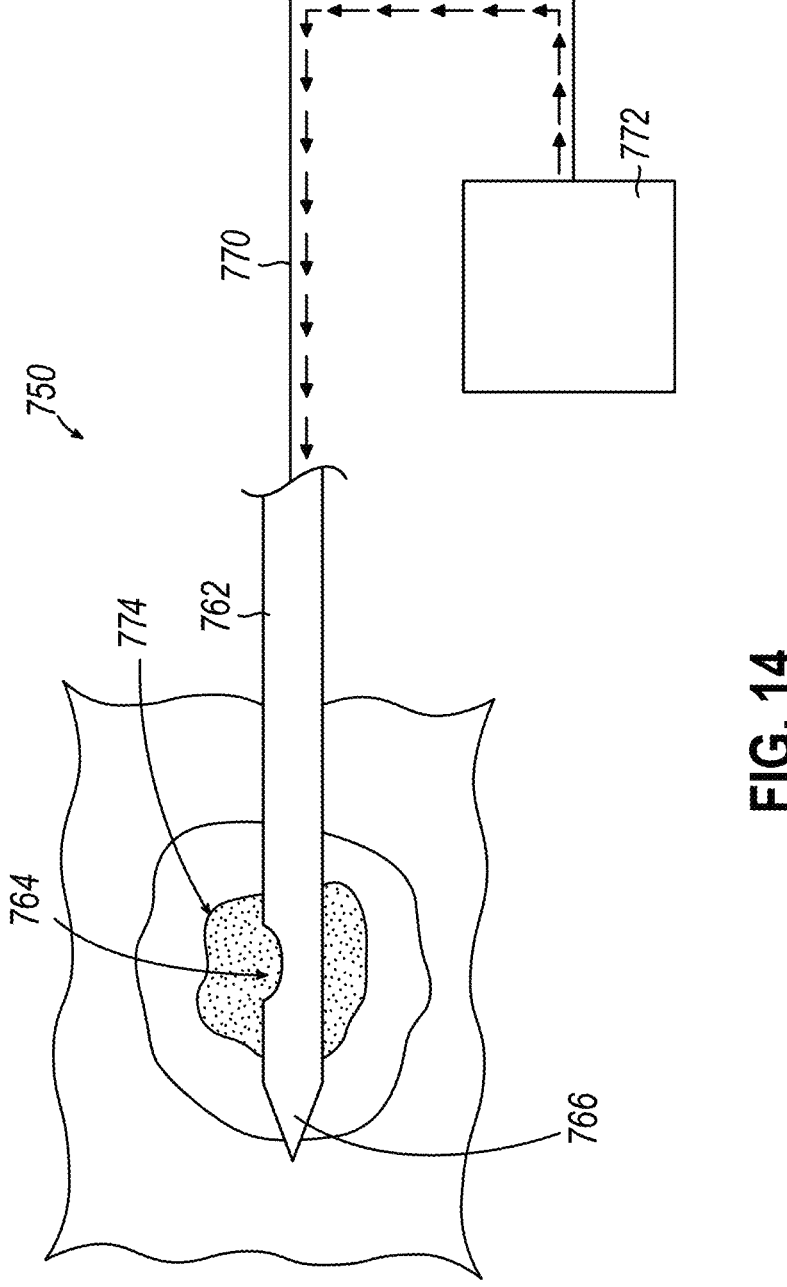
FIG. 14 depicts yet another side elevational view of the marker delivery device of FIG. 12, with the marker delivery device deploying a marking material.

As shown in FIG. 14, once outer cannula (762) is positioned at a targeted biopsy site, fluid source (722) can be used to inject a marking fluid (774) though outer cannula (762) out of side opening (764) and into the tissue. In the present example, marking fluid (774) includes a plurality of micro-beads, nano-beads, microspheres, and/or nanospheres configured to provide visibility under imaging such as ultrasound, x-ray, and/or MRI. In other examples, marking fluid (774) can include a gel such as hydrogel configured to change physical properties over time due to fluid absorption or other processes. In still other examples, marking fluid (774) includes a stain or other fluid that is configured to color or otherwise increase the visibility of the marked to tagged tissue. Regardless of the particular material used as marking fluid (774), marking fluid (774) exits side opening (764) and penetrates the tissue near side opening (764) to mark the area targeted for biopsy sampling.

Figure 15:
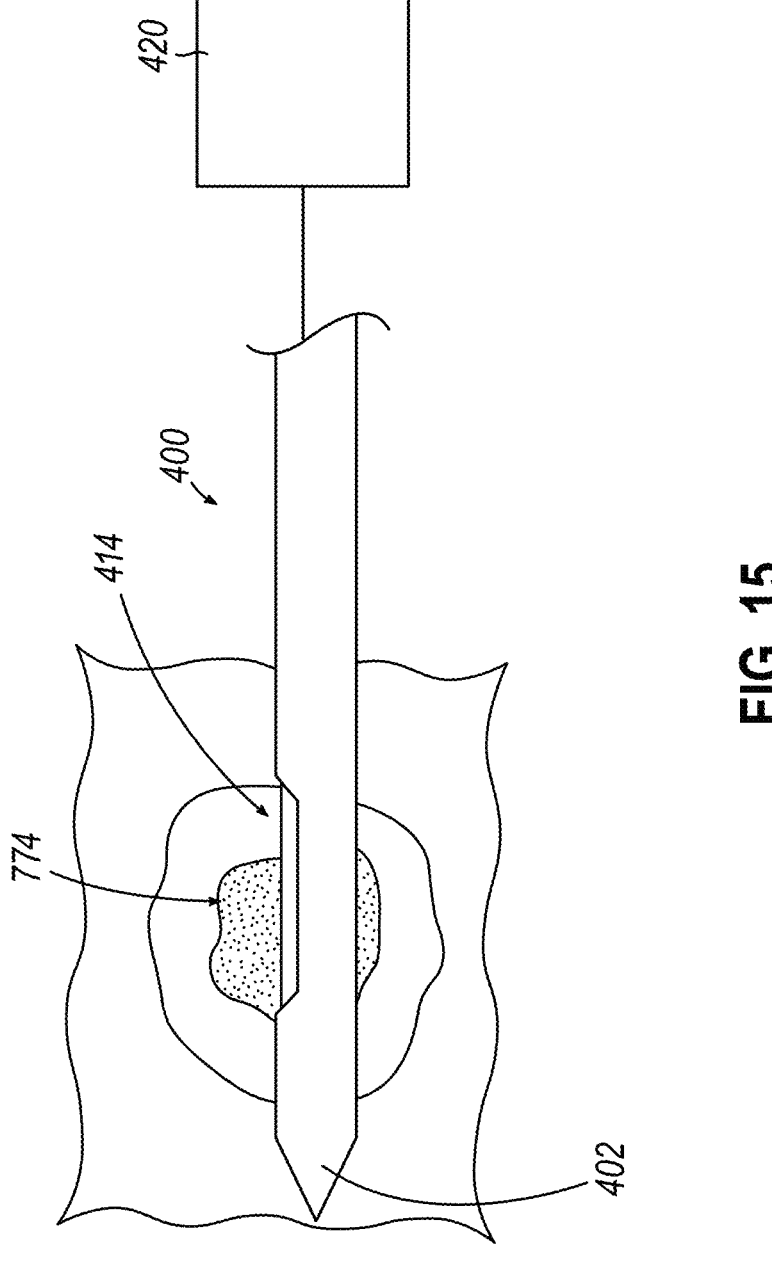
FIG. 15 depicts a side elevational view of the biopsy needle of FIG. 4 disposed within tissue to collect a biopsy sample.

Once marking is complete using marker delivery device (750), outer cannula (762) can be withdrawn from the tissue. As seen in FIG. 15, once outer cannula (762) is withdrawn, outer cannula (762) can be replaced with biopsy needle (400). Biopsy needle (400) can be connected to various biopsy device components (420). To assist with removal and storage of tissue samples collected from the area targeted for biopsy sampling. Once a suitable number of tissue samples are collected, biopsy needle (400) can be removed, leaving behind at least some marking fluid (774) for later identification of the biopsy site.

F. Exemplary Marker Delivery Device with Articulation

Figure 16:
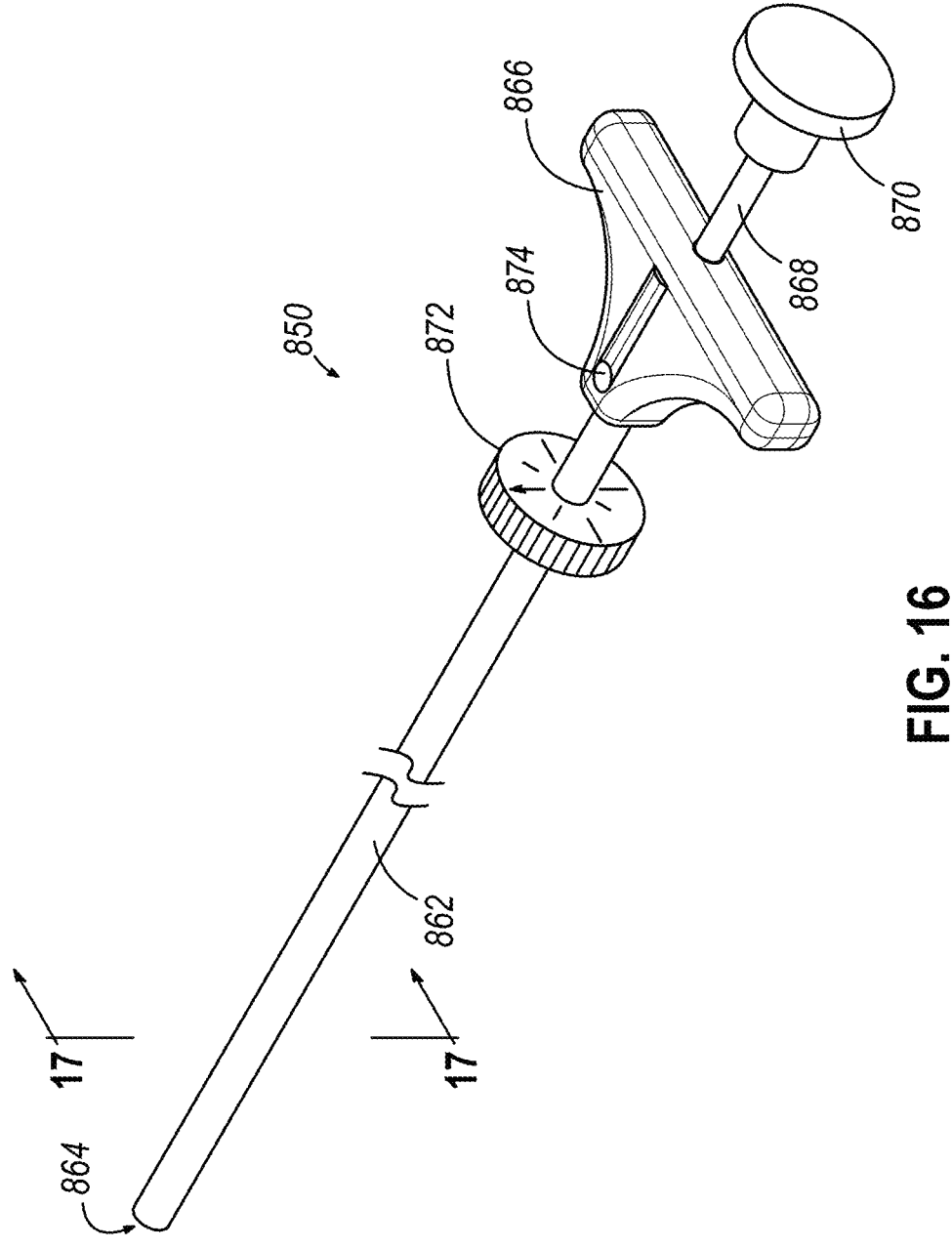
FIG. 16 depicts a perspective view of still another exemplary marker delivery device.

FIG. 16 shows an exemplary marker delivery device (850) that can be readily used with a marker (800) similar to marker (500) or any other marker described herein. Marker delivery device (850) of the present example is substantially similar to marker delivery device (150) described above except as otherwise noted herein. For instance, like marker delivery device (150), marker delivery device (850) of the present example includes an elongate outer cannula (862). Marker delivery device (850) likewise includes a grip (866) at the proximal end of cannula (862). Similarly, a push rod (868) (FIG. 17) similar to push rod (168) can be provided. Like with push rod (168), push rod (868) extends coaxially within cannula (862) such that push rod (868) is configured to translate within cannula (862) to displace one or more markers. A plunger (870) is coupled at the proximal end of rod (868) for forcing rod (868) distally in cannula (862) to deploy a marker out of cannula (862).

Unlike marker delivery device (150), marker delivery device (850) of the present example is generally configured as an end-deploy device rather than a side-deploy device. In particular, outer cannula (862) defines an open distal end (864) that is used as a marker exit in lieu of a side opening similar to side opening (164). Such a configuration can be desirable in contexts were marking occurs through an introducer with an open distal end rather than a needle similar to biopsy needle (400). For instance, in such configurations the open distal end of the introducer can be positioned with close proximity to a biopsy site and a marker can be deployed through the open distal end of the introducer. This configuration can generally be desirable to make marking simpler and to reduce the potential for error. As will be described in greater detail below, marker delivery device (850) of the present example can also be used in contexts where a marker is deployed though a lateral aperture of a biopsy needle similar to lateral aperture (414) described above.

It should be understood that, in some examples, outer cannula (862) can include certain features configured to hold a marker within outer cannula (862). For instance, in some examples, outer cannula (862) can include an inward taper at open distal end (864). In other examples, outer cannula (862) can include one or more bumps, dimples, ridges, ribs, and/or etc. In such examples, suitable bumps, dimples, ridges, and/or ribs can be elastomeric or rubberized to permit a marker to pass through open distal end (864), while also holding the marker therein. In still other examples, various alternative configurations will be apparent to those of ordinary skill in the art in view of the teachings herein.

Marker delivery device (850) also differs from marker delivery device (150) in the presence of a thumbwheel or rotation knob (872) and an actuator (876). As will be described in greater detail below, one or more internal components of marker delivery device (850) are configured to move at least a portion of outer cannula (862) between a straight configuration and a bent configuration. To facilitate this functionality, thumbwheel (872) of the present example is generally configured to permit an operator to select a clock position for the bending of outer cannula (862). Similarly, actuator (876) is generally configured to permit an operator to drive outer cannula (862) between the straight configuration and the bent configuration.

Thumbwheel (872) of the present example is generally configured as a round wheel that is rotatable relative to grip (866). Thumbwheel (872) includes a plurality of position indicators (874) that are configured to permit an operator to quickly identify the clock position of thumbwheel (872). As will be described in greater detail below, thumbwheel (872) is configured to rotate various internal components of marker delivery device (850) to control the direction of bending of outer cannula (862). Thus, position indicators (874) can provide an indication to an operator as to which direction outer cannula (862) will bend based on clock positions. In other words, an operator can select a variety of bending directions such as towards twelve o'clock (vertical), towards three o'clock (right looking at the page), towards six o'clock (down), towards nine o'clock (left looking at the page), and any other clock position in between. In some examples, thumbwheel (872) can include a plurality of grip features. In addition, it should be understood that although the present example includes thumbwheel (872), in other examples, thumbwheel (872) is entirely optional and may be omitted.

Actuator (876) of the present example is generally configured as a slider to longitudinally pull one or more components of marker delivery device (850) to move outer cannula (862) between the straight configuration and the bent configuration. To promote ease of use, actuator (876) is integrated into a portion of grip (866). However, it should be understood that in other examples (876) actuator (876) can be integrated into other components of marker delivery device (850) or be entirely separate such as a tethered remote control. Although the present example of actuator (876) generally involves manual actuation, it should be understood that in other examples actuator (876) can be configured as a motor or an electromechanical linear actuator. In such examples, actuator (876) can be remotely operated by a push button, dial, switch, or other electromechanical input means.

Figure 17:
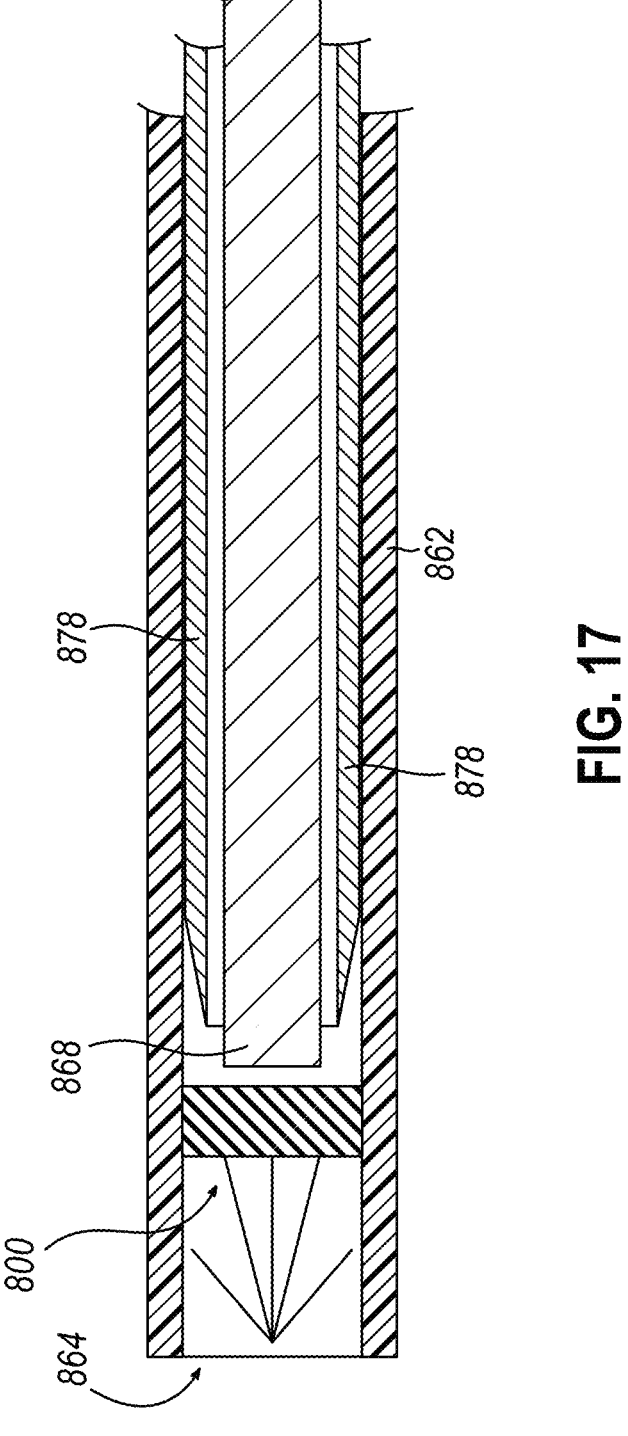
FIG. 17 depicts a side cross-sectional view of the marker delivery device of FIG. 16, with the cross-section taken along line 17-17 of FIG. 16.

Marker delivery device (850) further differs from marker delivery device (150) in the configuration of push rod (868). As best seen in FIG. 17, push rod (868) generally includes a similar configuration as with push rod (168) described above. However, unlike push rod (168), push rod (868) of the present example is separated from inner cannula (862) by a plurality of articulators (878). As will be described in greater detail below, articulators (878) are generally configured to move the combination of push rod (868) and outer cannula (862) to selectively bend or otherwise articulate a portion of push rod (868) and outer cannula (862). Despite this bending action, it should be understood that push rod (868) is still configured to translate relative to outer cannula (862) and articulators (878) even when in the bent configuration.

Articulators (878) can take on a variety of forms while promoting being of outer cannula (862) and translation of push rod (868). For instance, in the present example, articulators (878) can be configured as elongate wire rods or arms with a distal end secured or otherwise coupled to a portion of the interior of outer cannula (862). Thus, in the present configuration, each articulator (878) can be independently tensioned to control bending of outer cannula (862). Although only two articulators (878) are visible in the present FIGS., it should be understood that marker delivery device (850) can include a plurality of articulators (878). For instance, in some examples, marker delivery device (850) can include an articulator (878) for each clock position associated with thumbwheel (872).

Although not show, it should be understood that each articulator (878) can be operatively coupled to both thumbwheel (872) and actuator (876). For instance, actuator (876) can be operatively connected to each articulator (878) to selectively apply tension to a selected one or more articulators (878). Likewise, thumbwheel (872) can be operatively connected to each articulator (878) to selectively control which articulator (878) or set of articulators (878) receives tension from actuator (876). Thus, thumbwheel (872) and actuator (876) are configured to operate together to control both bending of outer cannula (862) and the direction of bending by controlling how tension is applied to articulators (878).

Figure 18:
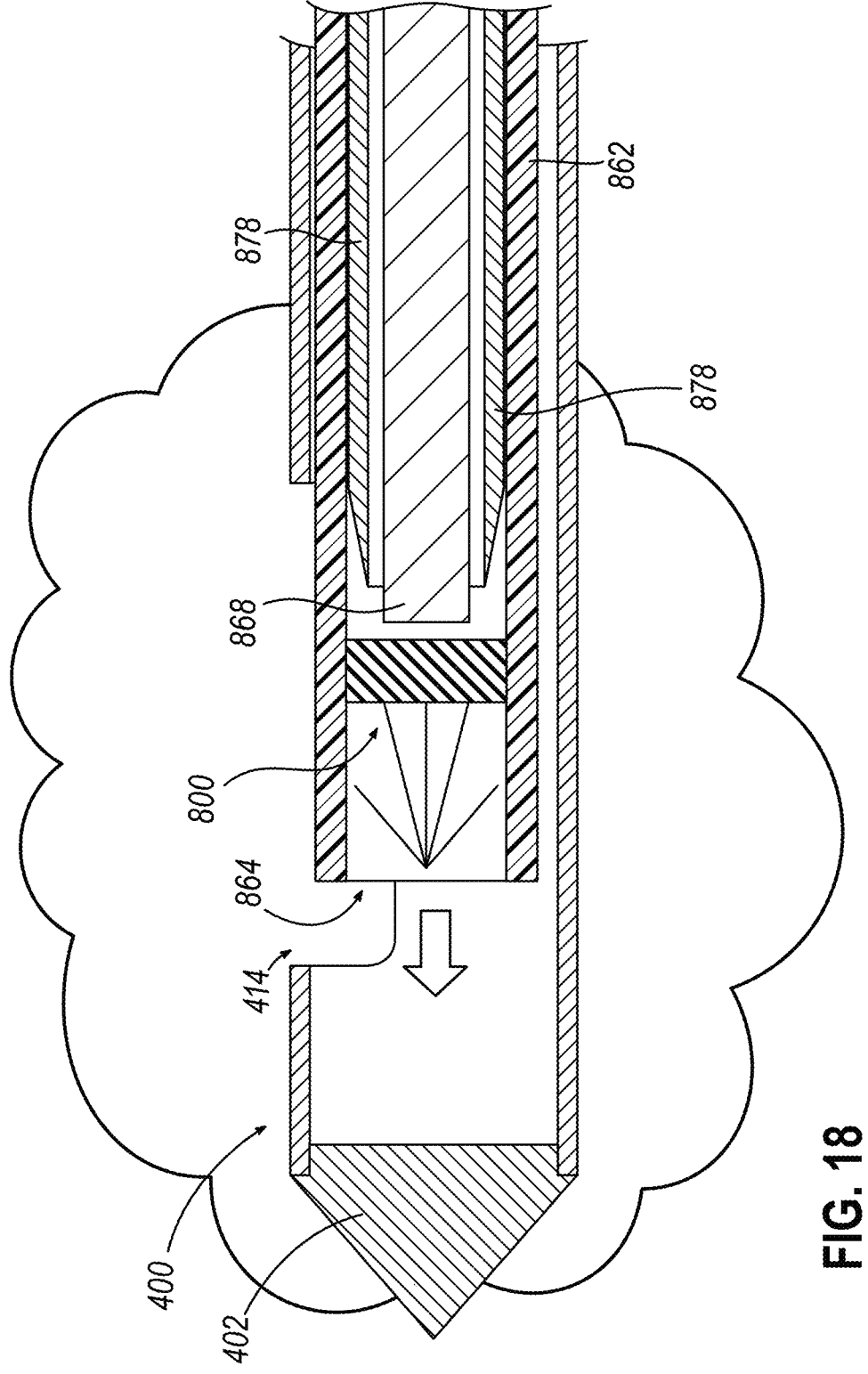
FIG. 18 depicts another side cross-sectional view of the marker delivery device of FIG. 16, with the marker delivery device being inserted into the biopsy needle of FIG. 4.
Figure 19:
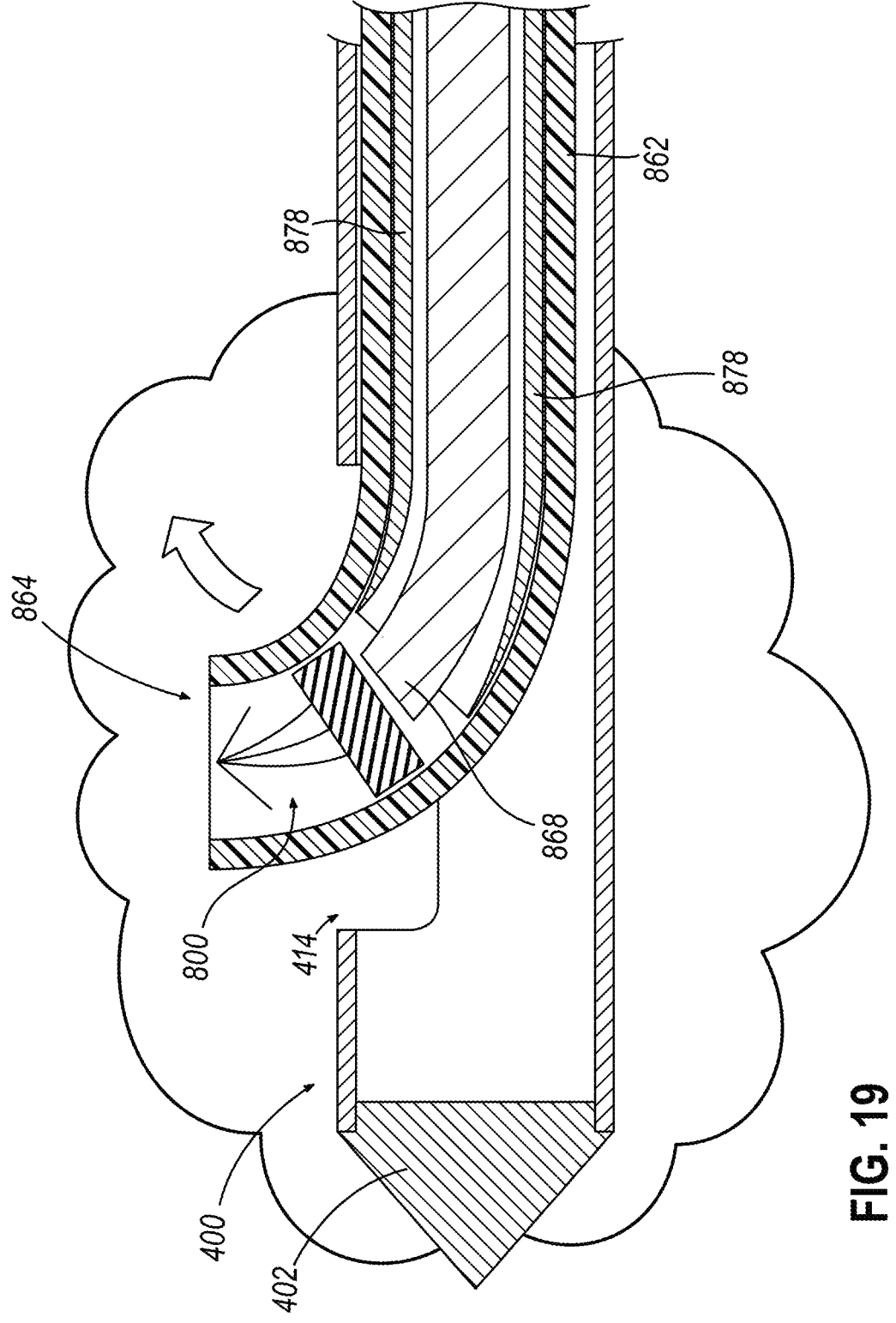
FIG. 19 depicts yet another side cross-sectional view of the marker delivery device of FIG. 16, with the marker delivery device in an articulated configuration.

FIGS. 18 and 19 show an exemplary use of marker delivery device (850) in connection with marker (800). It should be understood that marker (800) of the present example is substantially similar to marker (500) described above. Although marker delivery device (850) of the present example is shown as being used with marker (800), it should be understood that in other examples marker delivery device (850) can be readily used with any other suitable marker including, but not limited to, markers described herein.

Marker delivery device (850) initially begins in a loaded configuration. In the loaded configuration, marker (800) is disposed within outer cannula (862) of marker delivery device (850). In some examples, at least a portion of maker (800) can also seal against a portion of outer cannula (862) to prevent ingress of fluid into outer cannula (662). Also in the loaded configuration, outer cannula (862) is positioned in the straight configuration.

As can be seen in FIG. 18, when marker delivery device (850) is in the loaded configuration, outer cannula (862) can be inserted into biopsy needle (400). In the present use, this insertion occurs after biopsy needle (400) has been used to extract a tissue sample from a targeted region within tissue. Thus, biopsy needle (400) is already positioned at the biopsy site such that insertion of outer cannula (862) into biopsy needle (400) likewise positions outer cannula (862) at the biopsy site.

Although outer cannula (862) is shown as being used with biopsy needle (400) in the present use, it should be understood that, in some uses, introduction of marker delivery device (850) can be with performed without the aid of an introducer cannula, and/or other associated device. Regardless of the particular use, positioning of open distal end (864) can be confirmed using one or more forms of imaging guidance such as x-ray, ultrasound, MRI, and/or etc.

Once outer cannula (862) of marker delivery device (850) is positioned within tissue via biopsy needle (400), outer cannula (862) can be transitioned from the straight configuration to the bent configuration using actuator (876). The transition from the straight configuration to the bent configuration can be seen by comparing FIGS. 18 and 19. In particular, actuator (876) is pulled or otherwise actuated to tension one or more articulators (878) positioned within outer cannula (862). This tension then causes outer cannula (862) to bend or otherwise articulate, which also causes push rod (868) to bend. As can be seen in FIG. 19, this bending action causes open distal end (864) of outer cannula (862) to be positioned at the biopsy site though lateral aperture (414) of biopsy needle (400).

Figure 20:
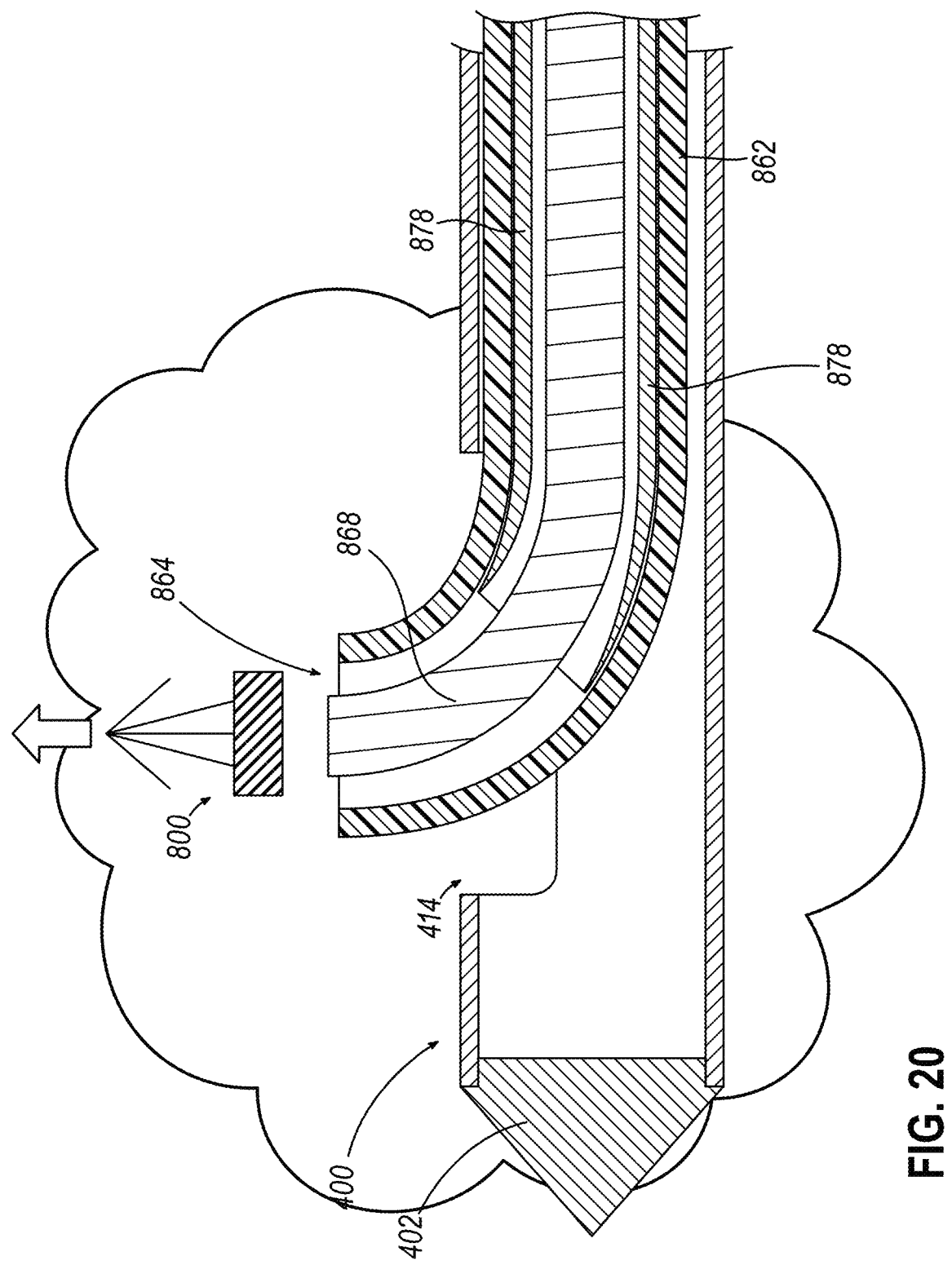
FIG. 20 depicts still another side cross-sectional view of the marker delivery device of FIG. 16, with the marker delivery device in a deployed position.

As can be seen in FIG. 20, once outer cannula (862) is in the bent configuration, marker (800) can be deployed through open distal end (864). To deploy marker (800), an operator can push plunger (870) to translate push rod (868) distally. In some uses, this can be accomplished using a single hand with the aid of grip (866). As push rod (868) is advanced distally, the distal end of push rod (868) engages marker (800) and pushes marker (800) out of open distal end (864). Outer cannula (862) of marker delivery device (850) can then be returned to the straight position and withdrawn from biopsy needle (400), leaving behind marker (800).

Once marker delivery device (850) is withdrawn from biopsy needle (400), one or more additional markers similar to marker (800) can be optionally deployed either with marker delivery device (850) (after reloading) or other marker delivery devices similar to marker delivery device (850).

G. Exemplary Marker Delivery Device with Distal Suction

Figure 21:
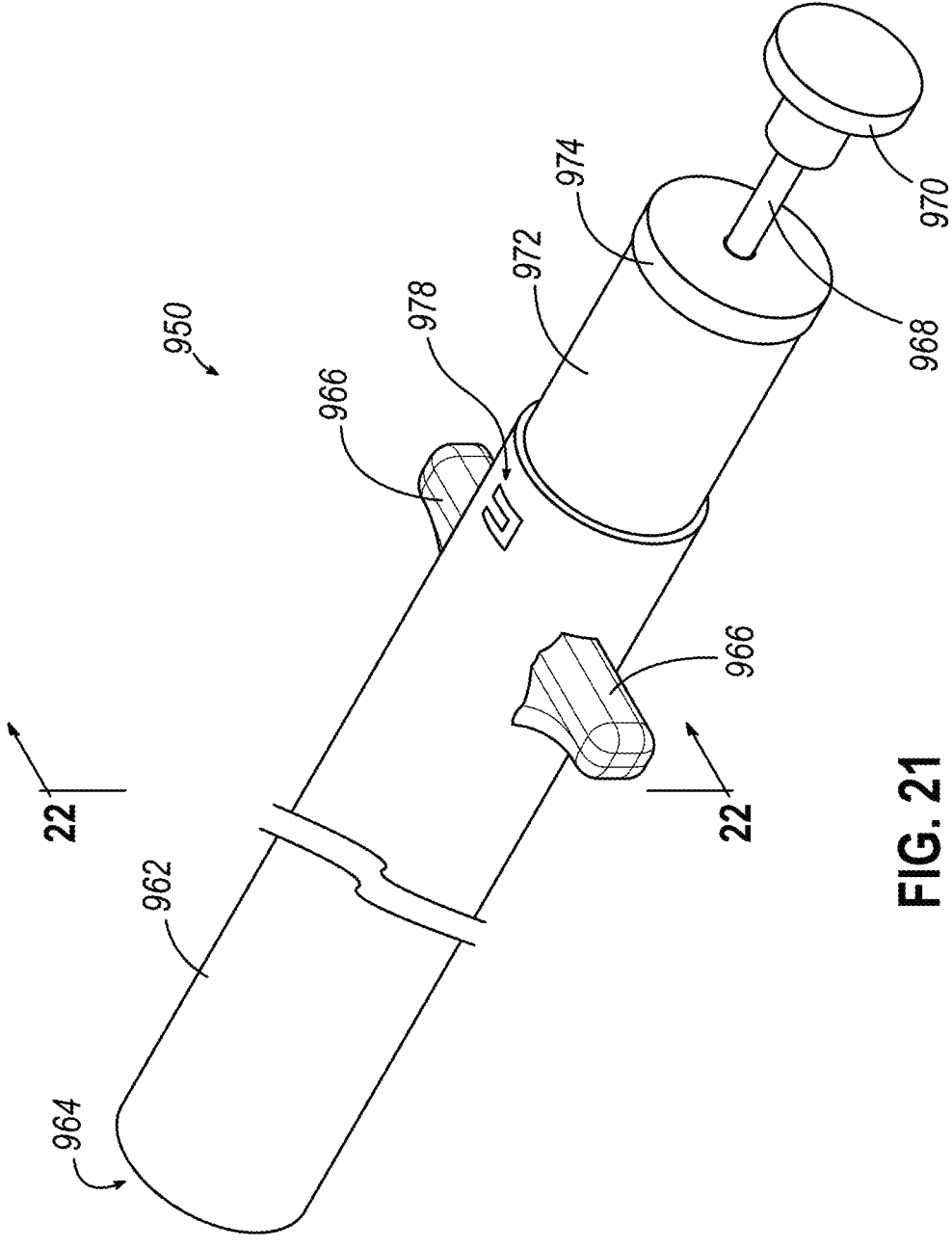
FIG. 21 depicts a perspective view of still another exemplary marker delivery device.

FIG. 21 shows an exemplary marker delivery device (950) that can be readily used with a marker (900) substantially similar to marker (500) or any other marker described herein. Marker delivery device (950) of the present example is substantially similar to marker delivery device (150) described above except as otherwise noted herein. For instance, like marker delivery device (150), marker delivery device (950) of the present example includes an elongate outer cannula (962). Marker delivery device (950) likewise includes a grip (966) at the proximal end of cannula (962). Similarly, a push rod (968) similar to push rod (168) can be provided. Like with push rod (168), push rod (968) extends coaxially within cannula (962) such that push rod (968) is configured to translate within cannula (962) to displace one or more markers. A plunger (970) is coupled at the proximal end of rod (968) for forcing rod (968) distally in cannula (962) to deploy a marker.

Unlike marker delivery device (150), marker delivery device (950) of the present example is generally configured as an end-deploy device rather than a side-deploy device. In particular, outer cannula (962) defines an open distal end (964) that is used to receive tissue for marking purposes in lieu of a side opening similar to side opening (164). As will be described in greater detail below, open distal end (964) is configured to receive tissue when a negative pressure is applied to outer cannula (962). The issue is then marked while disposed within outer cannula (962) through open distal end (964). Such a configuration can be desirable in contexts were marking occurs through an introducer with an open distal end rather than a needle similar to biopsy needle (400). For instance, in such configurations the open distal end of the introducer can be positioned with close proximity to a biopsy site and a marker can be deployed through the open distal end of the introducer. This configuration can generally be desirable to make marking simpler and to reduce the potential for error.

Marker delivery device (950) also differs from marker delivery device (150) in the that marker delivery device (950) includes an inner tube (972). Inner tube (972) is an elongate tube sized to correspond to about the size of the inner diameter of outer cannula (962). Inner tube (972) is generally movable within outer cannula (962) independently of outer cannula (962) and push rod (968). As will be described in greater detail below, inner tube (972) is generally configured to induce a vacuum or negative fluid pressure within outer cannula (962) to draw tissue into outer cannula (962) through open distal end (964).

Inner tube (972) includes a cap (974) on the proximal end thereof. Cap (974) is generally sized to promote manipulation of inner tube (972) to pull inner tube (972) proximally relative to outer cannula (962). As seen in FIG. 21, cap (974) generally provides a lip or protrusion beyond the outer diameter of inner tube (972) that can be used for gripping purposes. In other examples, cap (974) can have a variety of forms that can include additional features to enhance grip. By way of example only, in some examples cap (974) can be configured similarly to grip (966).

Figure 22:
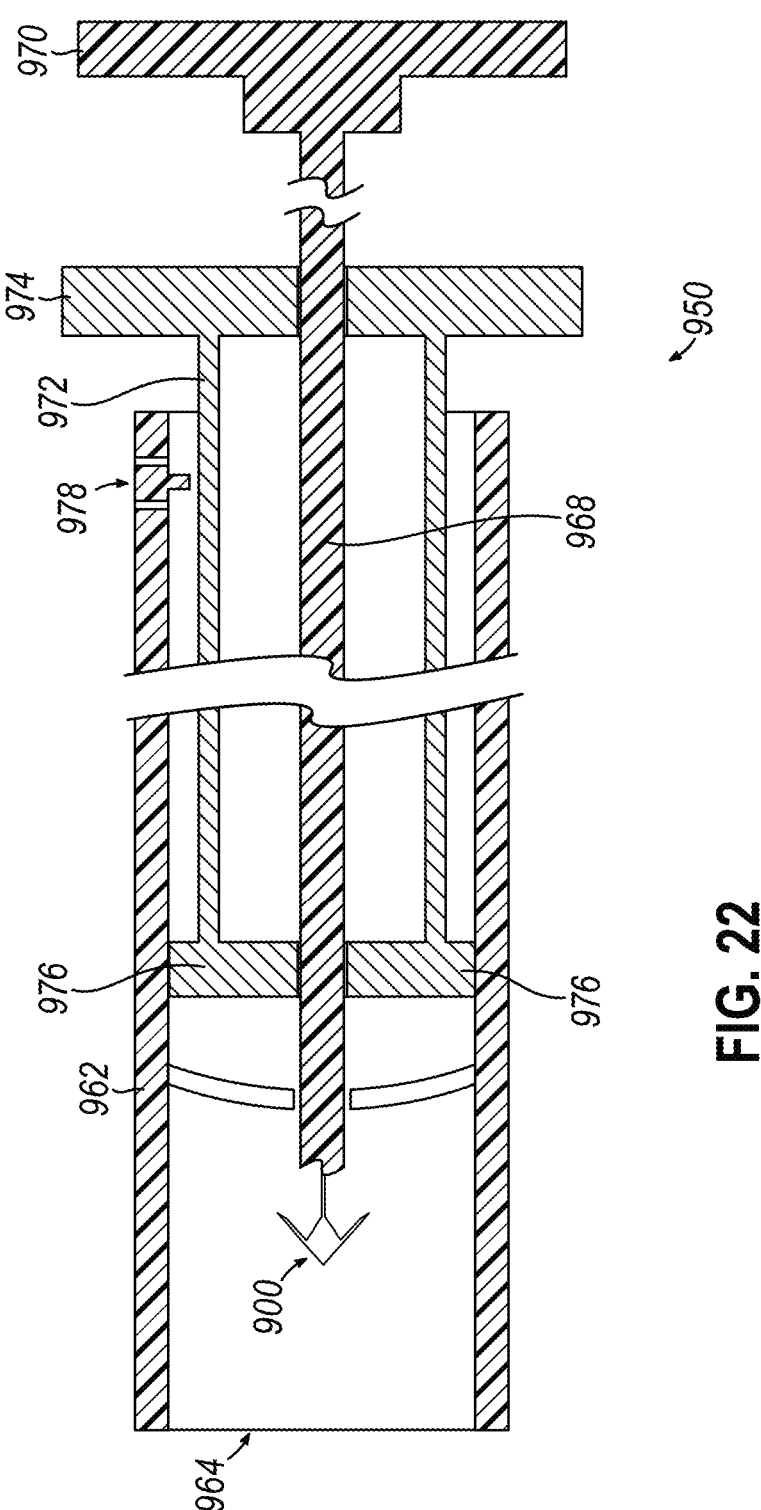
FIG. 22 depicts a side cross-sectional view of the marker delivery device of FIG. 21, with the cross-section taken along line 22-22 of FIG. 21.

As best seen in FIG. 22, the distal end of inner tube (972) includes one or more seals (976) configured to seal against the inner diameter of outer cannula (962). As will be described in greater detail below, this sealing configuration permits inner tube (972) to act as a syringe or piston-like mechanism to generate vacuum distally of seals (976) when inner tube (972) is pulled proximally. It should be understood that seals (976) can take on a variety of forms. For instance, in some examples, seals (972) include one or more rubber or elastomeric O-rings or disks wrapped around the end of inner tube (972). In other examples, seals (972) are formed by a portion of inner tube (972) being rubberized. Of course, various alternative sealing configurations will be apparent to those of ordinary skill in the art in view of the teachings herein. In addition, in still other examples inner tube (972) can be replaced entirely by a separate independent vacuum source such as a vacuum pump coupled to outer cannula (962) with a tube or catheter.

As will be described in greater detail below, proximal movement of inner tube (972) is used to prepare tissue for marking. Because of this, it may be desirable to lock inner tube (972) into position relative to outer cannula (962) after inner tube (972) has been moved proximally to a predetermined proximal position. Accordingly, outer cannula (962) of the present example is shown as including a lock (978) configured to engage inner tube (972) once inner tube (972) reaches a predetermined proximal position. Lock (978) in the present example is configured as a resilient tab that is integral with outer cannula (962). In some examples, lock (978) can flex as seals (976) pass lock (978). Lock (978) can then engage seals (976) to hold inner tube (972) in position. Although the present example is shown as including only one lock (978), it should be understood that multiple locks (978) of a similar or different configuration can be used. In addition, it should be understood that lock (978) can take on a variety of forms (e.g., detent, resilient arms, snap fits, magnetic locks, and/or etc.) that can be integral with outer cannula (962) or entirely separate therefrom.

Push rod (968) generally extends through the center of inner tube (972). As discussed above, inner tube (972) is generally independently movable relative to push rod (968). Thus, any interface between inner tube (972) and push rod (968) is generally configured to movability of push rod (968) relative to inner tube (972) and/or inner tube (972) relative to push rod (968). In addition, it should be understood that portions of inner tube (972) can be configured to seal against the exterior of push rod (968) so as to not interfere with vacuum generated by inner tube (972). In some examples, such sealing can be accomplished using sealing features described above with respect to seals (976) of inner tube (972).

FIGS. 23 through 26 show an exemplary use of marker delivery device (950) in connection with marker (900). It should be understood that marker (900) of the present example is substantially similar to marker (500) described above. Although marker delivery device (950) of the present example is shown as being used with marker (900), it should be understood that in other examples marker delivery device (950) can be readily used with any other suitable marker including but not limited to markers described herein.

Figure 23:
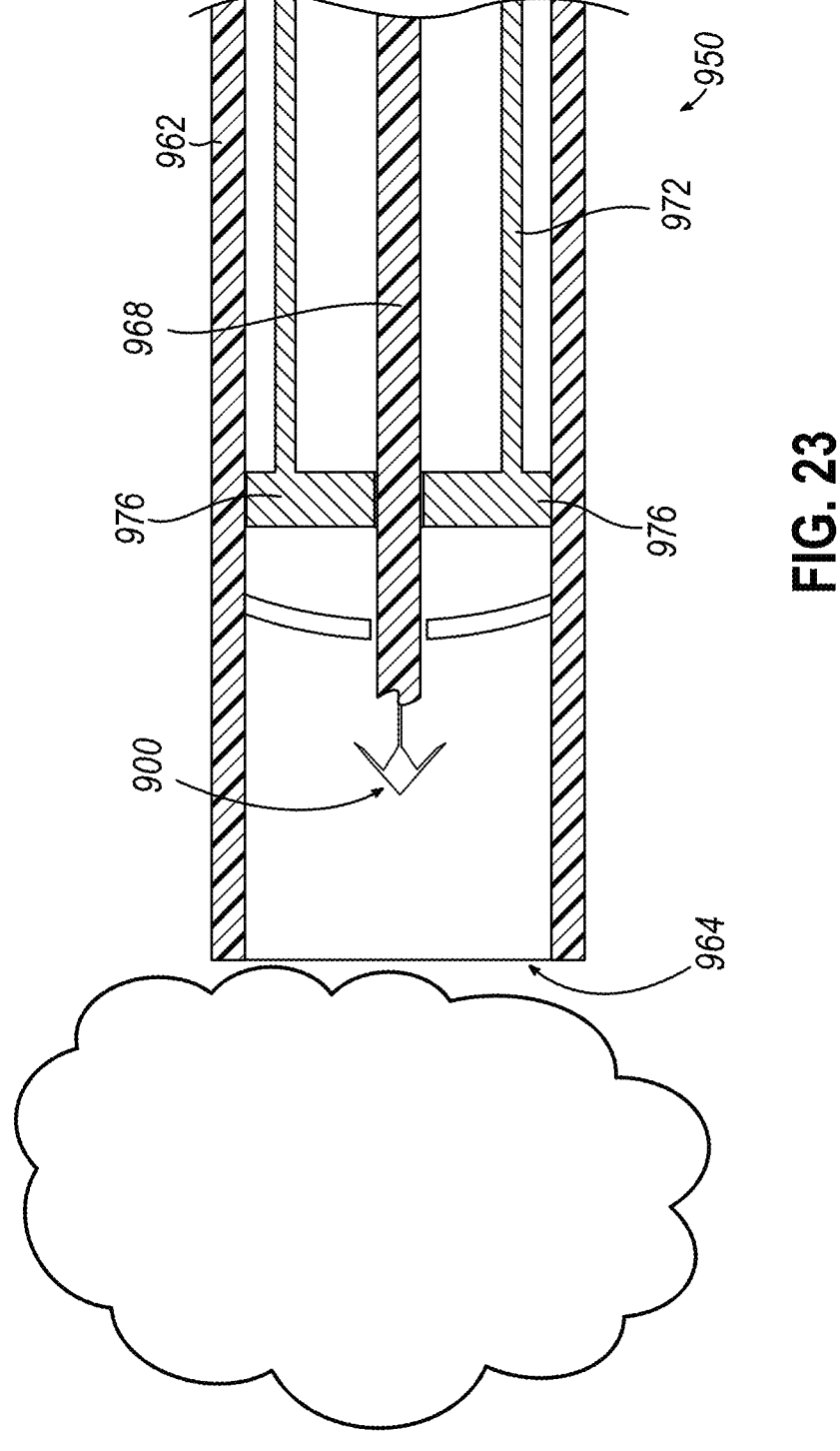
FIG. 23 depicts another side cross-sectional view of the marker delivery device of FIG. 21, with the marker delivery device in a loaded configuration.

As seen in FIG. 23, marker delivery device (950) initially begins in a loaded configuration. In the loaded configuration, marker (900) is disposed within outer cannula (962) of marker delivery device (950), just inside open distal end (964). In addition, at least a portion of maker (900) is configured to couple to the distal end of push rod (968). In some examples, this coupling can be accomplished via a crimp-type mechanism similar to crimp (622) described above with respect to marker (600). In other examples, this coupling can be accomplished via an interference fit between marker (900) a bore or opening within push rod (968). Regardless, push rod (968) is positioned proximally within outer cannula (962) to define at least some space between marker (900) and open distal end (964). As will be described in greater detail below, this space generally defines a volume that can be used to receive tissue within outer cannula (962).

While marker delivery device (950) is in the loaded configuration, outer cannula (962) marker delivery device (950) can be inserted into tissue of a patient to position open distal end (964) at a biopsy site. In some uses, introduction of marker delivery device (950) can be with performed without the aid of an introducer cannula, biopsy needle, or other associated device. In other uses, introduction of marker delivery device (950) can be performed through a biopsy needle similar to biopsy needle (400) described above. In still other uses, introduction of marker delivery device (950) can be performed with the aid of an introducer cannula used in connection with a biopsy needle or other associated device. In all uses, positioning of open distal end (964) can be confirmed using one or more forms of imaging guidance such as x-ray, ultrasound, MRI, and/or etc.

Figure 24:
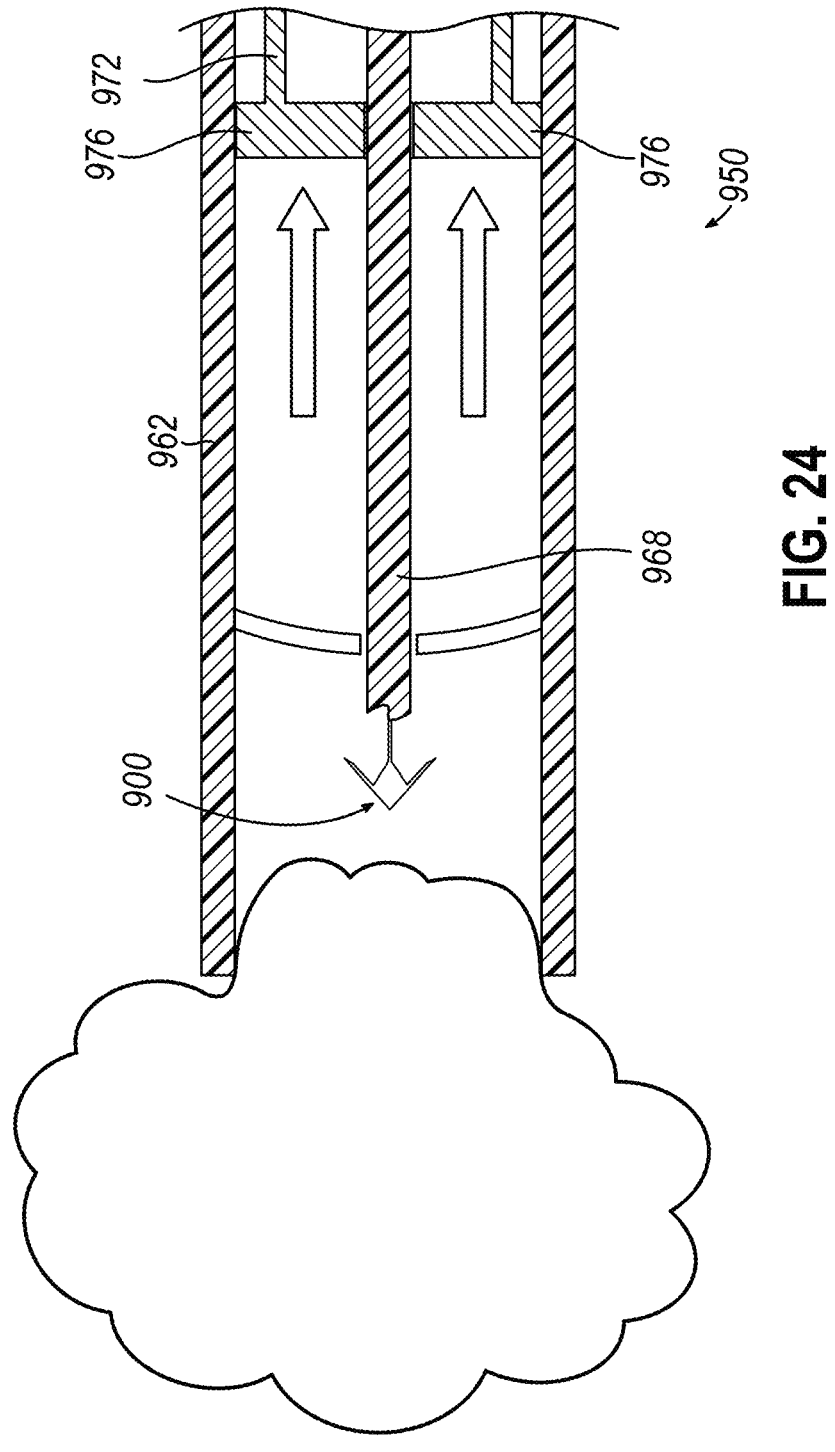
FIG. 24 depicts yet another side cross-sectional view of the marker delivery device of FIG. 21, with the marker delivery device in a tissue collection configuration.

Once outer cannula (962) of marker delivery device (950) is positioned within tissue, marker (900) can be deployed using open distal end (964). In particular, as seen in FIG. 24, deployment begins by retracting inner tube (972) proximally relative to outer cannula (962) and push rod (968). The retraction of inner tube (972) induces vacuum within outer cannula (962) distally of seals (976). This vacuum causes at least some tissue to be pulled into outer cannula (962) through open distal end (964).

Figure 25:
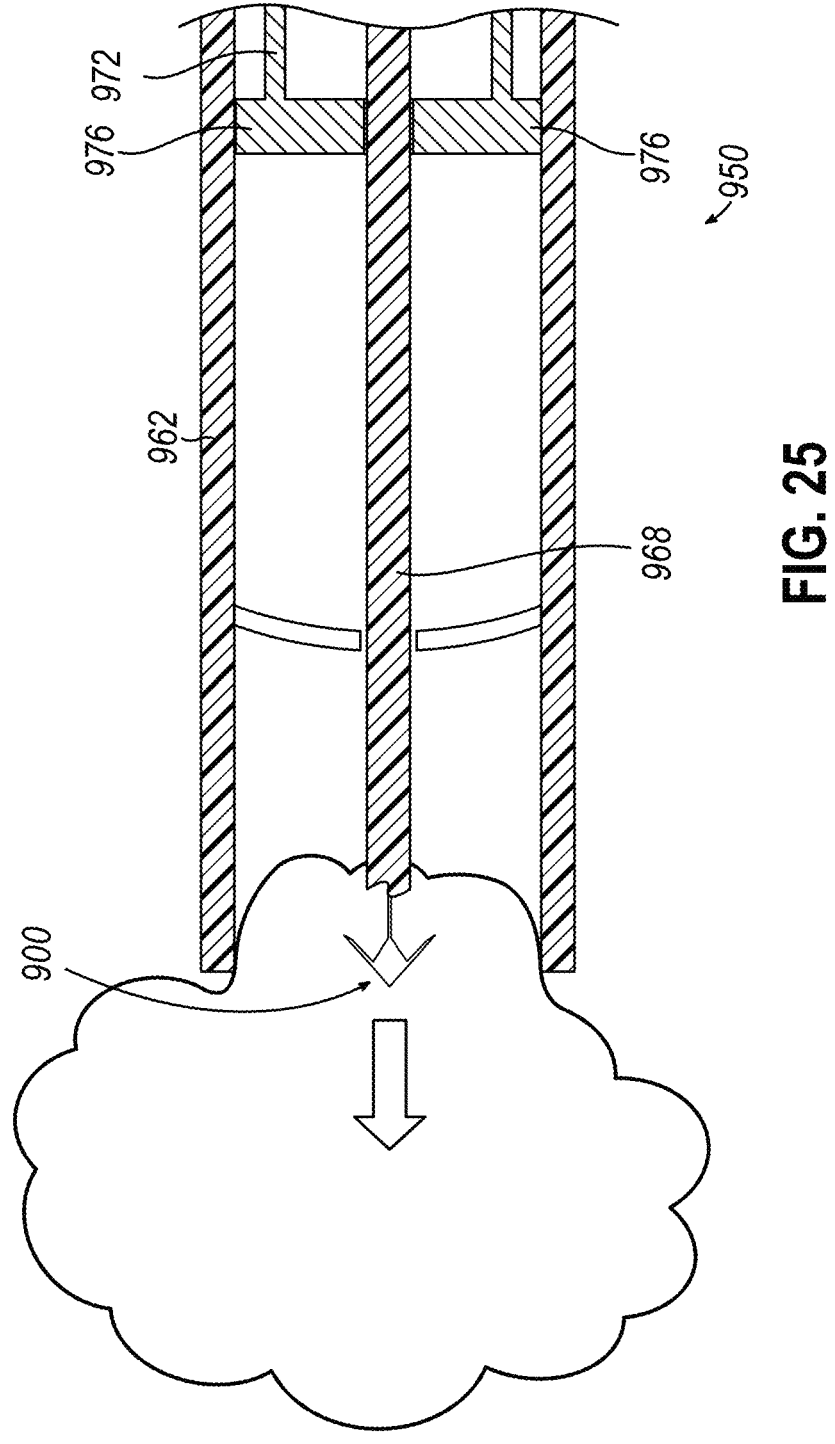
FIG. 25 depicts still another side cross-sectional view of the marker delivery device of FIG. 21, with the marker delivery device in a deployed configuration.

Once tissue is pulled into outer cannula (962) through open distal end (964), push rod (968) can be used to deploy marker (900) into tissue. In particular, as seen in FIG. 25, push rod (968) is advanced distally relative to outer cannula (962) and inner tube (972). This advancement causes marker (900) to penetrate into the tissue that was previously pulled into outer cannula (962). Due to barbs, arms, hooks, or other geometry, marker (900) can then be stuck or otherwise coupled to the tissue.

Figure 26:
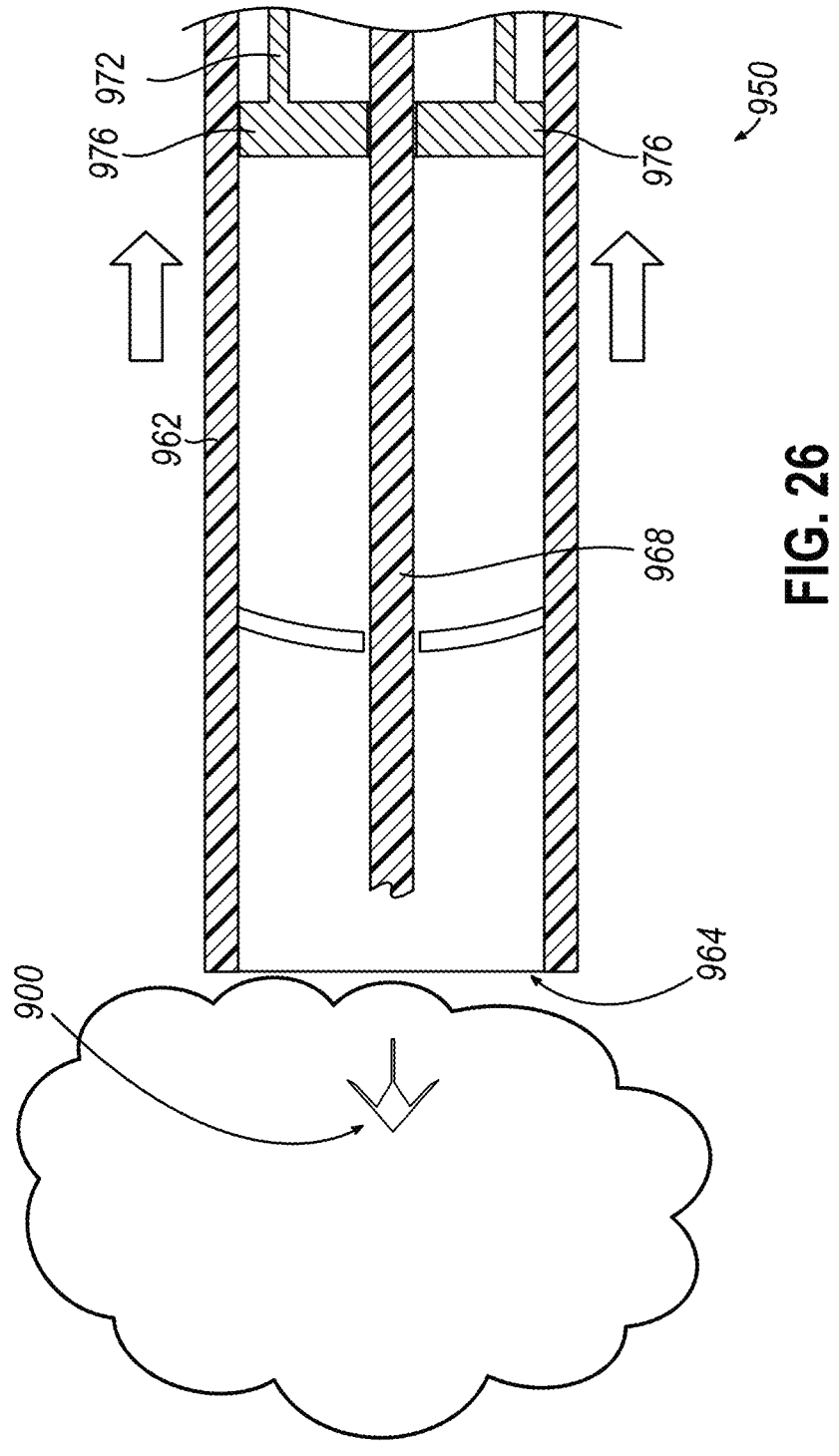
FIG. 26 depicts still another side cross-sectional view of the marker delivery device of FIG. 21, with the marker delivery device being withdrawn.

Once marker (900) is deployed into the tissue, push rod (968) can be retracted proximally relative to outer cannula (962), thereby leaving marker (900) behind within the tissue. Inner tube (972) can then be advanced distally to release the vacuum pressure, thereby releasing the tissue from outer cannula (962). Once the tissue is released, outer cannula (962) can be withdrawn from the patient as shown in FIG. 26. At this stage, one or more additional markers similar to marker (900) can be optionally deployed either with marker delivery device (950) (after reloading) or other marker delivery devices similar to marker delivery device (950).

H. Exemplary Marker Delivery Device with Side Suction

Figure 27:
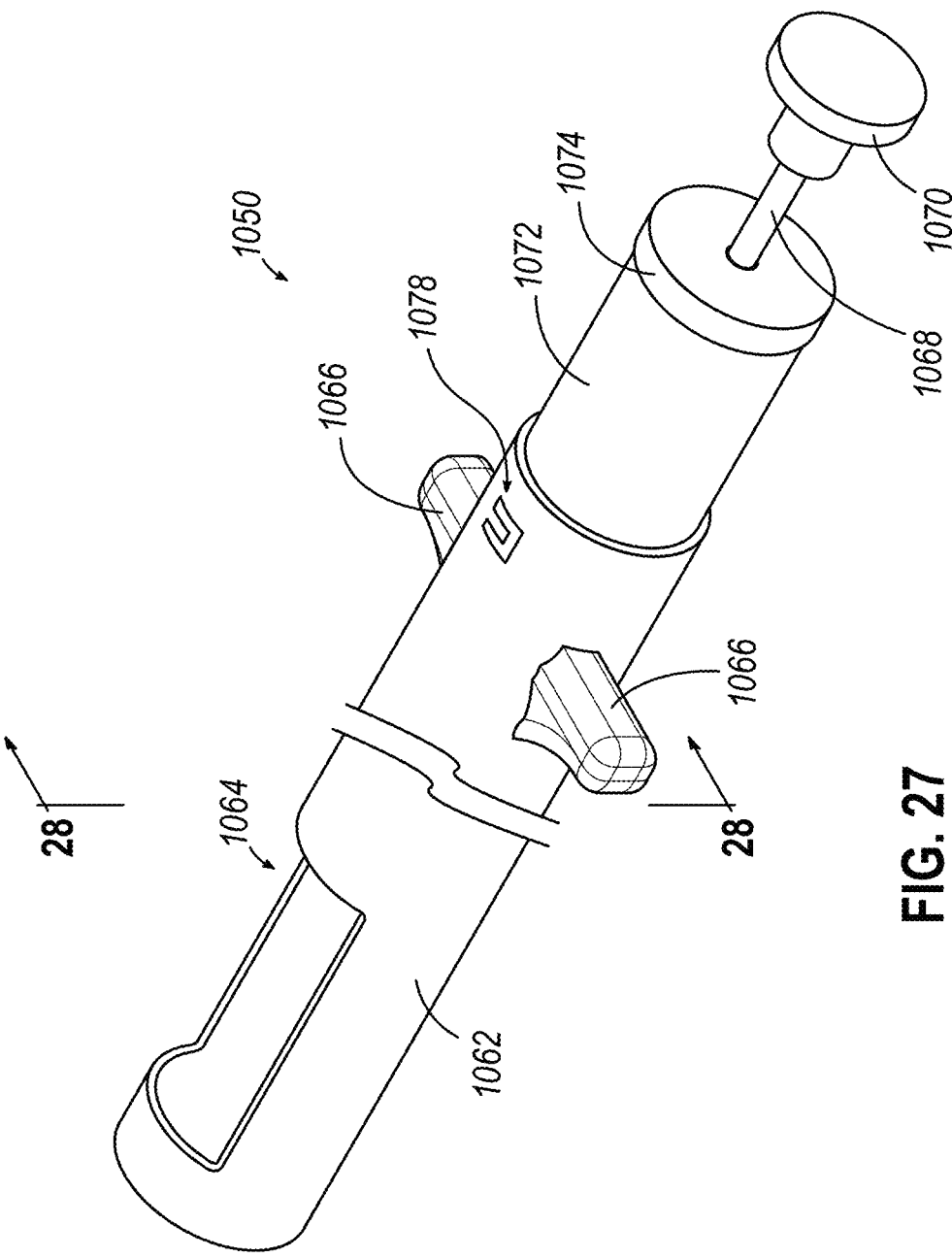
FIG. 27 depicts a perspective view of still another exemplary marker delivery device.

FIG. 27 shows an exemplary marker delivery device (1050) that can be readily used with a marker (1000) substantially similar to marker (500) or any other marker described herein. Marker delivery device (1050) of the present example is substantially similar to marker delivery device (150) described above except as otherwise noted herein. For instance, like marker delivery device (150), marker delivery device (1050) of the present example includes an elongate outer cannula (1062). Marker delivery device (1050) likewise includes a grip (1066) at the proximal end of cannula (1062). Similarly, a push rod (1068) similar to push rod (168) can be provided. Like with push rod (168), push rod (1068) extends coaxially within cannula (1062) such that push rod (1068) is configured to translate within cannula (1062) to displace one or more markers. A plunger (1070) is coupled at the proximal end of rod (1068) for forcing rod (1068) distally in cannula (1062) to deploy a marker.

Like marker delivery device (150), marker delivery device (1050) of the present example is generally configured as a side-deploy device. In particular, outer cannula (1062) defines a side opening (1064) similar to side opening (164) that can be used as a marker exit. However, unlike side opening (164), side opening (1064) of the present example is generally oversized such that side opening (1064) is configured to receive tissue for marking purposes. As will be described in greater detail below, side opening (1064) is configured to receive tissue when a negative pressure is applied to outer cannula (1062). The issue is then marked while disposed within outer cannula (1062) through side opening (1064). Such a configuration can be desirable in contexts were marking occurs through a needle similar to biopsy needle (400). For instance, in such configurations a lateral aperture similar to lateral aperture (414) can be aligned with a lesion or other target tissue. Side opening (1064) can then be aligned with the lateral aperture after the biopsy procedure is complete to accurately mark the biopsy site.

Marker delivery device (1050) also differs from marker delivery device (150) in the that marker delivery device (1050) includes an inner tube (1072). Inner tube (1072) is an elongate tube sized to correspond to about the size of the inner diameter of outer cannula (1062). Inner tube (1072) is generally movable within outer cannula (1062) independently of outer cannula (1062) and push rod (1068). As will be described in greater detail below, inner tube (1072) is generally configured to induce a vacuum or negative fluid pressure within outer cannula (1062) to draw tissue into outer cannula (1062) through side opening (1064).

Inner tube (1072) includes a cap (1074) on the proximal end thereof. Cap (1074) is generally sized to promote manipulation of inner tube (1072) to pull inner tube (1072) proximally relative to outer cannula (1062). As seen in FIG. 27, cap (1074) generally provides a lip or protrusion beyond the outer diameter of inner tube (1072) that can be used for gripping purposes. In other examples, cap (1074) can have a variety of forms that can include additional features to enhance grip. By way of example only, in some examples cap (1074) can be configured similarly to grip (1066).

Figure 28:
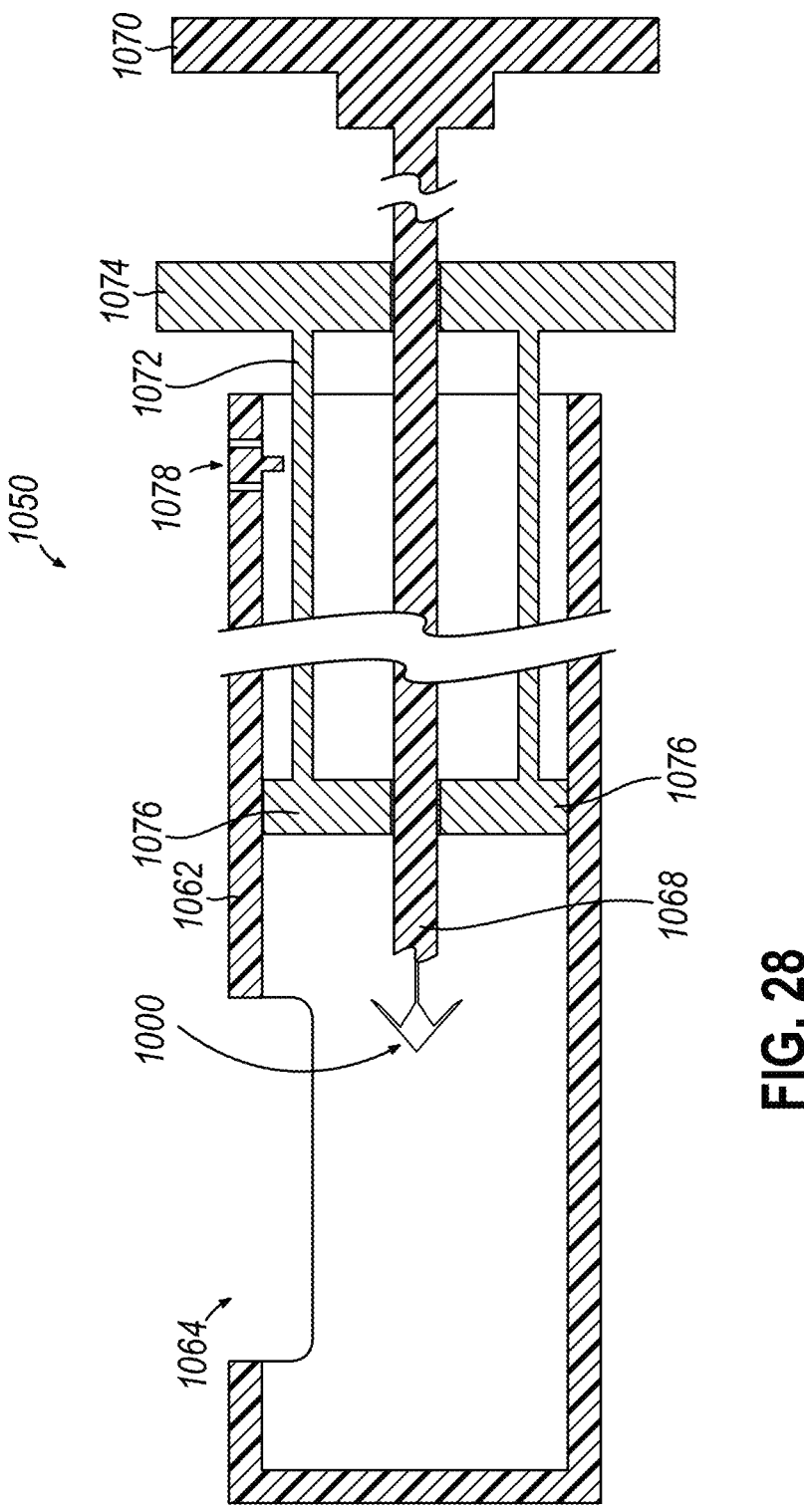
FIG. 28 depicts a side cross-sectional view of the marker delivery device of FIG. 27, with the cross-section taken along line 28-28 of FIG. 27.

As best seen in FIG. 28, the distal end of inner tube (1072) includes one or more seals (1076) configured to seal against the inner diameter of outer cannula (1062). As will be described in greater detail below, this sealing configuration permits inner tube (1072) to act as a syringe or piston-like mechanism to generate vacuum distally of seals (1076) when inner tube (1072) is pulled proximally. It should be understood that seals (1076) can take on a variety of forms. For instance, in some examples, seals (1072) include one or more rubber or elastomeric O-rings or disks wrapped around the end of inner tube (1072). In other examples, seals (1072) are formed by a portion of inner tube (1072) being rubberized. Of course, various alternative sealing configurations will be apparent to those of ordinary skill in the art in view of the teachings herein. In addition, in still other examples inner tube (1072) can be replaced entirely by a separate independent vacuum source such as a vacuum pump coupled to outer cannula (1062) with a tube or catheter.

As will be described in greater detail below, proximal movement of inner tube (1072) is used to prepare tissue for marking. Because of this, it may be desirable to lock inner tube (1072) into position relative to outer cannula (1062) after inner tube (1072) has been moved proximally to a predetermined proximal position. Accordingly, outer cannula (1062) of the present example is shown as including a lock (1078) configured to engage inner tube (1072) once inner tube (1072) reaches a predetermined proximal position. Lock (1078) in the present example is configured as a resilient tab that is integral with outer cannula (1062). In some examples, lock (1078) can flex as seals (1076) pass lock (1078). Lock (1078) can then engage seals (1076) to hold inner tube (1072) in position. Although the present example is shown as including only one lock (1078), it should be understood that multiple locks (1078) of a similar or different configuration can be used. In addition, it should be understood that lock (1078) can take on a variety of forms (e.g., detent, resilient arms, snap fits, magnetic locks, and/or etc.) that can be integral with outer cannula (1062) or entirely separate therefrom.

Push rod (1068) generally extends through the center of inner tube (972). As discussed above, inner tube (1072) is generally independently movable relative to push rod (1068). Thus, any interface between inner tube (1072) and push rod (1068) is generally configured to movability of push rod (1068) relative to inner tube (1072) and/or inner tube (1072) relative to push rod (1068). In addition, it should be understood that portions of inner tube (1072) can be configured to seal against the exterior of push rod (1068) so as to not interfere with vacuum generated by inner tube (1072). In some examples, such sealing can be accomplished using sealing features described above with respect to seals (1076) of inner tube (1072).

FIGS. 29 through 32 show an exemplary use of marker delivery device (1050) in connection with marker (1000). It should be understood that marker (1000) of the present example is substantially similar to marker (500) described above. Although marker delivery device (1050) of the present example is shown as being used with marker (1000), it should be understood that in other examples marker delivery device (1050) can be readily used with any other suitable marker including but not limited to markers described herein.

Figure 29:
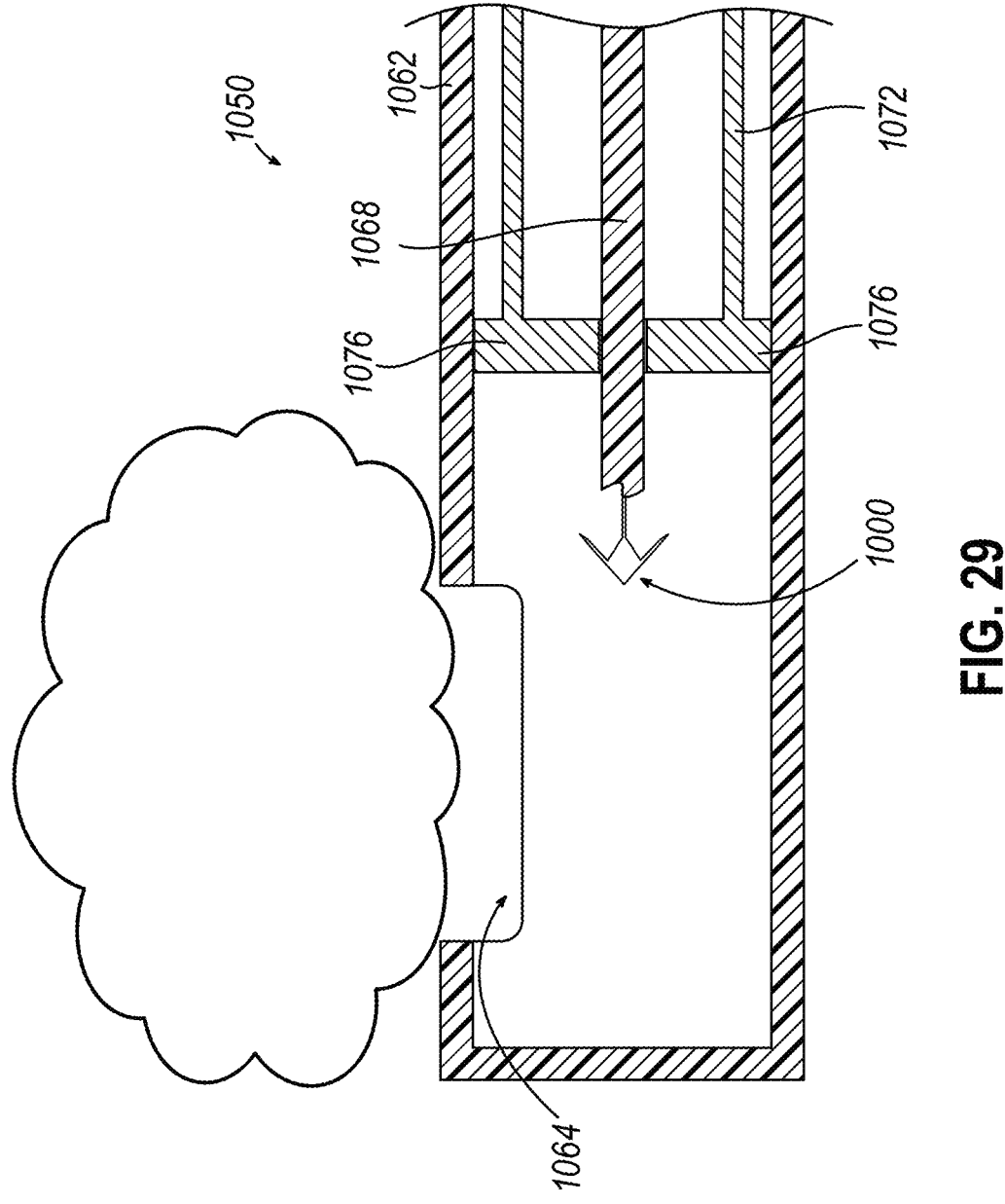
FIG. 29 depicts another side cross-sectional view of the marker delivery device of FIG. 27, with the marker delivery device in a loaded configuration.

As seen in FIG. 29, marker delivery device (1050) initially begins in a loaded configuration. In the loaded configuration, marker (1000) is disposed within outer cannula (1062) of marker delivery device (1050), just inside side opening (1064) and proximally of side opening (1064). In addition, at least a portion of maker (1000) is configured to couple to the distal end of push rod (1068). In some examples, this coupling can be accomplished via a crimp-type mechanism similar to crimp (622) described above with respect to marker (600). In other examples, this coupling can be accomplished via an interference fit between marker (1000) a bore or opening within push rod (1068). Regardless, push rod (1068) is positioned proximally within outer cannula (1062) to define at least some space between marker (1000) and side opening (1064). As will be described in greater detail below, this space generally defines a volume that can be used to receive tissue within outer cannula (1062).

While marker delivery device (1050) is in the loaded configuration, outer cannula (1062) marker delivery device (1050) can be inserted into tissue of a patient to position side opening (1064) at a biopsy site. In some uses, introduction of marker delivery device (1050) can be with performed through a biopsy needle similar to biopsy needle (400) described above. In other uses, introduction of marker delivery device (1050) can be performed with the aid of an introducer cannula used in connection with a biopsy needle or other associated device. In all uses, positioning of side opening (1064) can be confirmed using one or more forms of imaging guidance such as x-ray, ultrasound, MRI, and/or etc.

Figure 30:
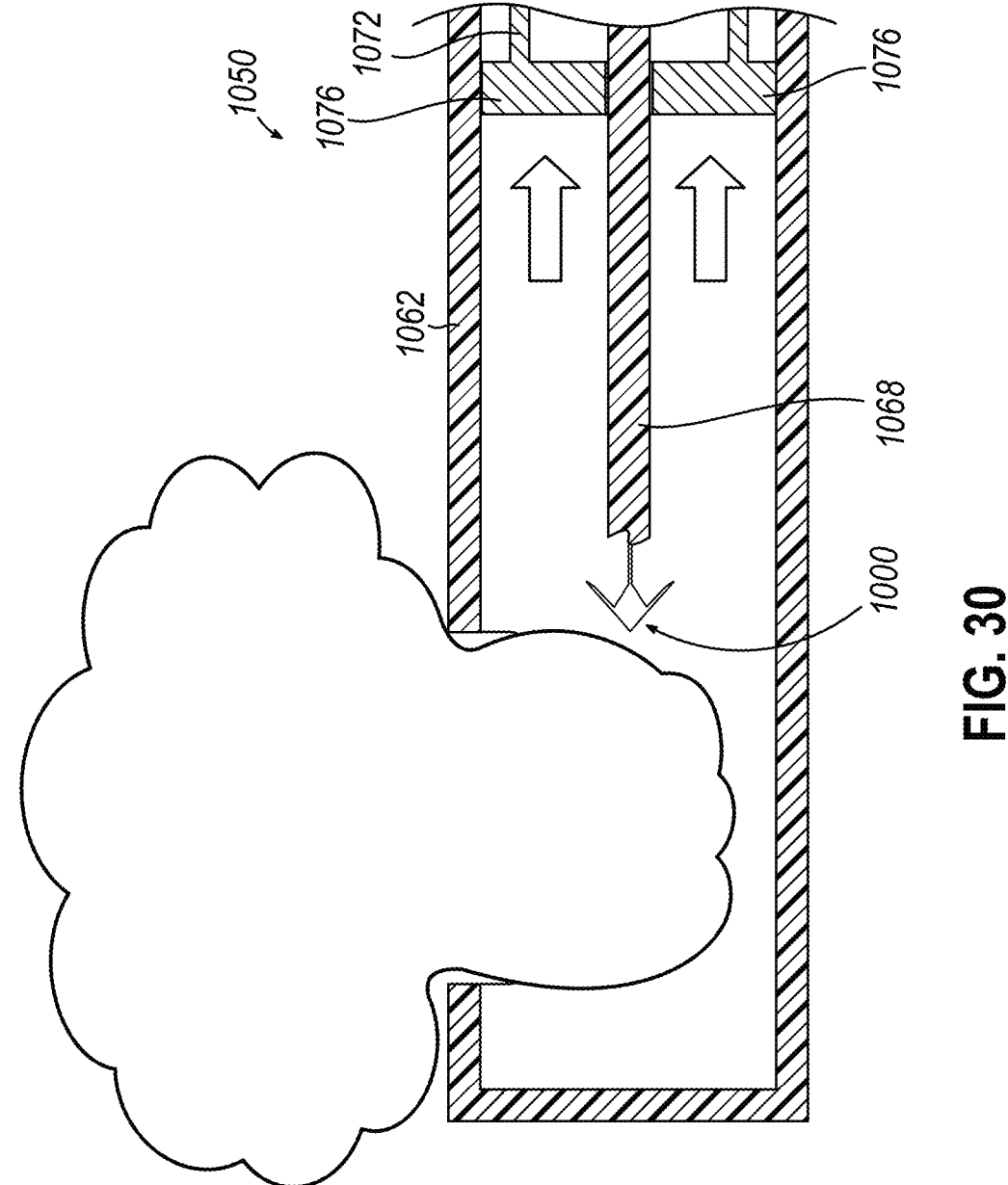
FIG. 30 depicts yet another side cross-sectional view of the marker delivery device of FIG. 27, with the marker delivery device in a tissue collection configuration.

Once outer cannula (1062) of marker delivery device (1050) is positioned within tissue, marker (1000) can be deployed using side opening (1064). In particular, as seen in FIG. 30, deployment begins by retracting inner tube (1072) proximally relative to outer cannula (1062) and push rod (1068). The retraction of inner tube (1072) induces vacuum within outer cannula (1062) distally of seals (1076). This vacuum causes at least some tissue to be pulled into outer cannula (1062) through side opening (1064).

Figure 31:
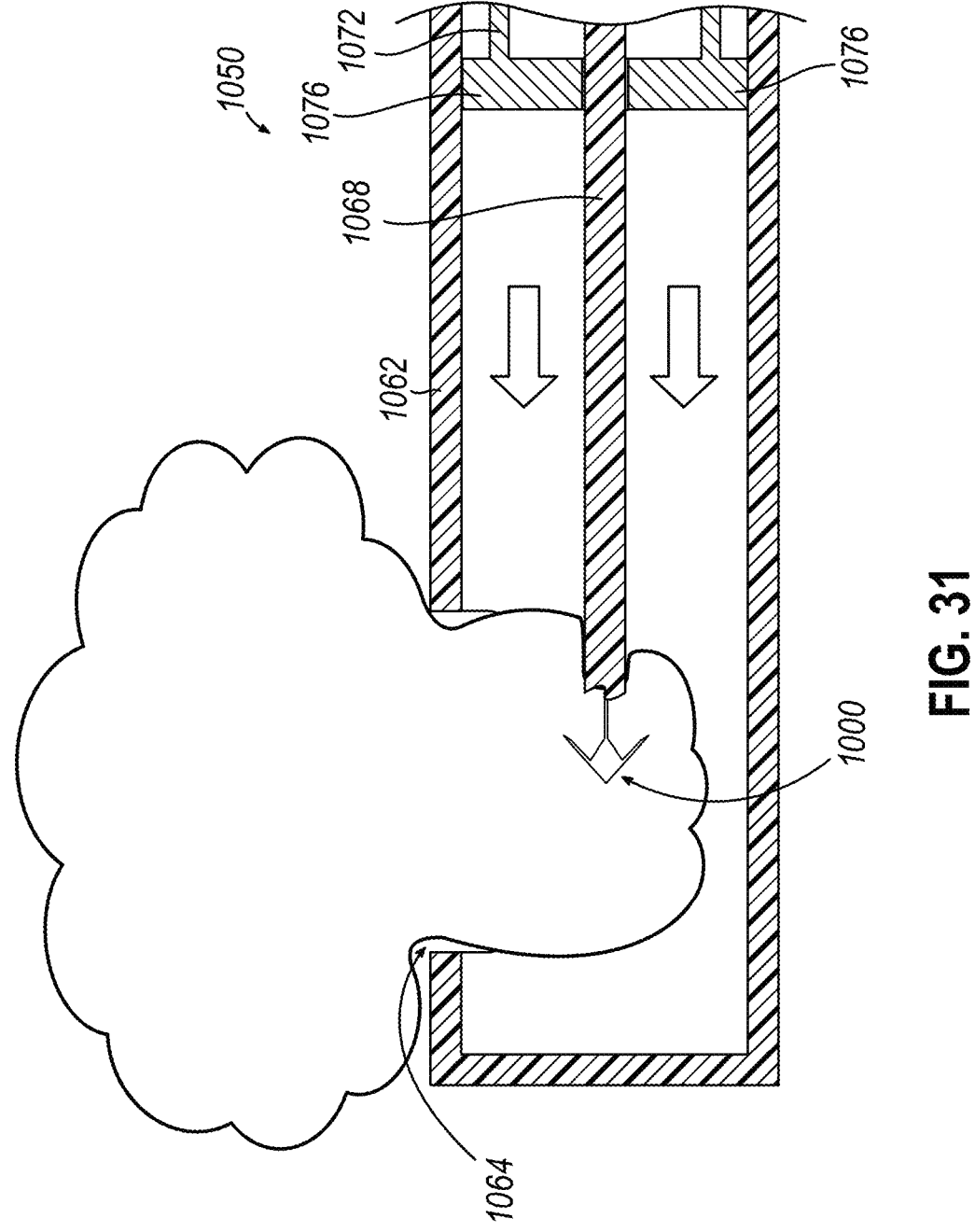
FIG. 31 depicts still another side cross-sectional view of the marker delivery device of FIG. 27, with the marker delivery device in a deployed configuration.

Once tissue is pulled into outer cannula (1062) through side opening (1064), push rod (1068) can be used to deploy marker (1000) into tissue. In particular, as seen in FIG. 31, push rod (1068) is advanced distally relative to outer cannula (1062) and inner tube (1072). This advancement causes marker (1000) to penetrate into the tissue that was previously pulled into outer cannula (1062). Due to barbs, arms, hooks, or other geometry, marker (1000) can then be stuck or otherwise coupled to the tissue.

Figure 32:
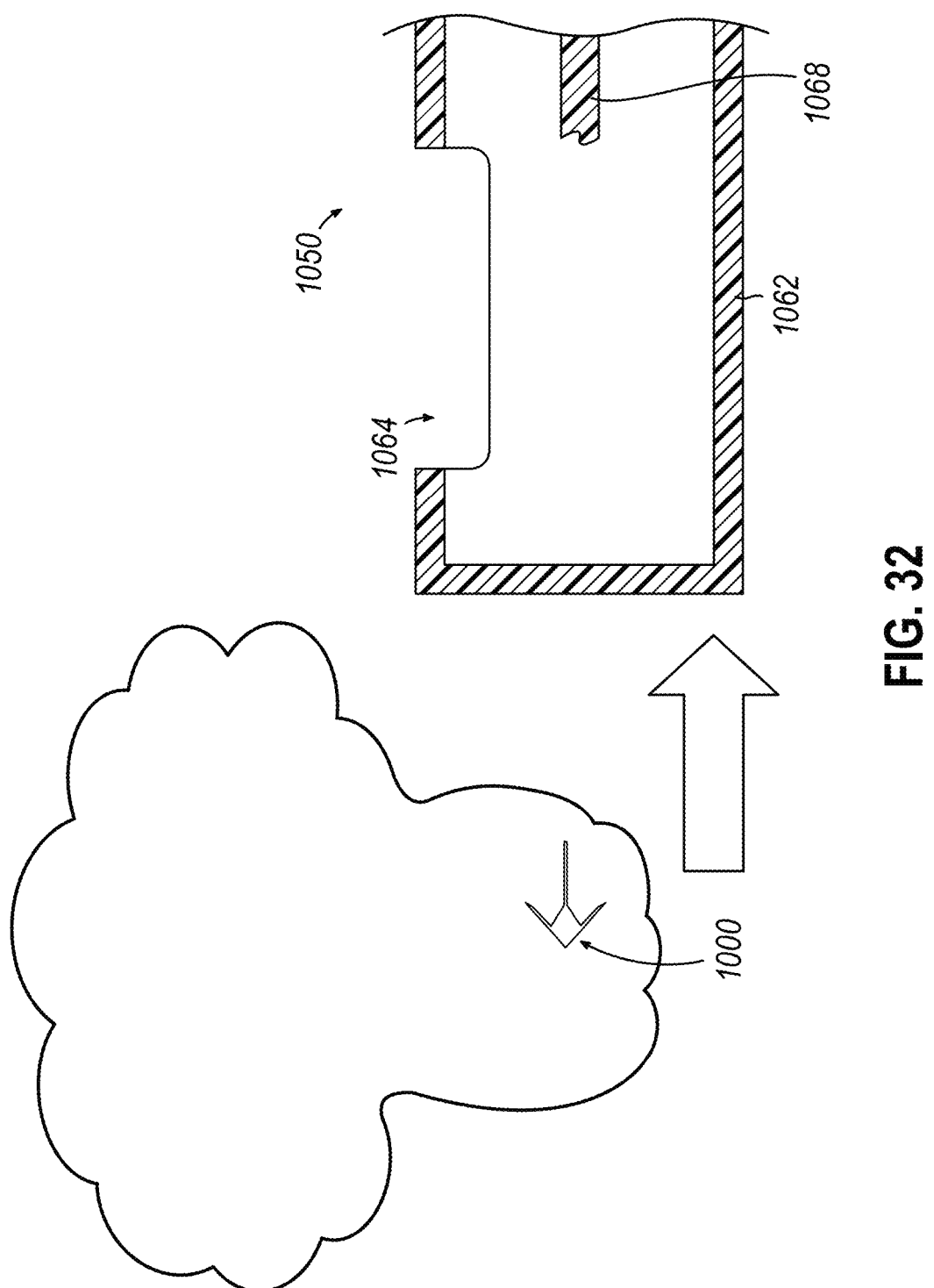
FIG. 32 depicts still another side cross-sectional view of the marker delivery device of FIG. 27, with the marker delivery device being withdrawn.

Once marker (1000) is deployed into the tissue, push rod (1068) can be retracted proximally relative to outer cannula (1062), thereby leaving marker (1000) behind within the tissue. Inner tube (1072) can then be advanced distally to release the vacuum pressure, thereby releasing the tissue from outer cannula (1062). Once the tissue is released, outer cannula (1062) can be withdrawn from the patient as shown in FIG. 32. At this stage, one or more additional markers similar to marker (1000) can be optionally deployed either with marker delivery device (1050) (after reloading) or other marker delivery devices similar to marker delivery device (1050).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: a grip; a cannula extending distally from the grip; a push rod configured to move within the cannula and having distal end with one or more seals configured to seal against an interior of the cannula; and a marker element having one or more barbs, wherein the push rod is configured to generate a pressure within the cannula between the one or more seals and the marker element to eject the marker element from the cannula.

Example 2

The marker delivery device of Example 1, wherein the cannula includes an open distal end configured to permit the marker element to exit therethrough.

Example 3

The marker delivery device of Example 1, wherein the cannula includes a side opening configured to permit the marker element to exit therethrough.

Example 4

The marker delivery device of any one or more of Examples 1 through 3, wherein the cannula includes a marker stop configured to releasably engage the marker.

Example 5

The marker delivery device of any one or more of Examples 1 through 4, wherein the one or more seals includes two seals.

Example 6

The marker delivery device of any one or more of Examples 1 through 5, wherein the one or more seals includes one or more O-rings.

Example 7

The maker delivery device of any one or more of Examples 1 through 6, wherein the marker element includes an outwardly projecting base configured to obstruct the flow of fluid through the cannula between the maker element and the interior of the base.

Example 8

The marker delivery device of any one or more of Examples 1 through 7, wherein the marker element further includes a sharp tip and one or more arms extending proximally and outwardly relative to the sharp tip.

Example 9

The marker delivery device of Example 8, wherein each arm defines a barb of the one or more barbs.

Example 10

The marker delivery device of any one or more of Examples 1 through 9, wherein the marker element is disposed within a carrier.

Example 11

A marker delivery device comprising: a grip; a cannula extending distally from the grip; a push rod configured to move within the cannula and having distal end; and a marker element having a body, one or more barbs, and a tether extending proximally from the body, wherein the tether is coupled to the distal end of the push rod, wherein the tether is configured to decouple from the push rod in response to distal movement of the push rod.

Example 12

The marker delivery device of Example 11, wherein the tether includes a crimp, wherein the crimp is configured to concentrate stress within a portion of the tether to break the tether at a predetermined position in response to distal movement of the push rod.

Example 13

The marker delivery device of Example 11, wherein the tether includes a stress concentrator configured to concentrate stress within a portion of the tether to break the tether at a predetermined position in response to distal movement of the push rod.

Example 14

The marker delivery device of any one or more of Examples 11 through 13, wherein the tether is integrally connected to the distal end of the push rod.

Example 15

The marker delivery device of any one or more of Examples 11 through 14, wherein the cannula includes an open distal end.

Example 16

The marker delivery device of Example 15, wherein the cannula is tapered at the open distal end, wherein at least a portion of the marker element is configured to rest on the open distal end outside the cannula.

Example 17

The marker delivery device of any one or more of Examples 11 through 16, wherein the marker element further includes a sharp tip and one or more arms extending proximally and outwardly relative to the sharp tip.

Example 18

The marker delivery device of Example 17, wherein the one or more arms are configured to engage a portion of the cannula such that a portion of the marker element is disposed outside the cannula and another portion of the marker element is disposed inside the cannula.

Example 19

The marker delivery device of any one or more of Examples 17 through 18, wherein the tether extends proximally from the sharp tip.

Example 20

The marker delivery device of any one or more of Examples 17 through 19, wherein each barb of the one or more barbs is defined by a corresponding arm of the one or more arms.

Example 21

A marker delivery device comprising: a grip; a cannula extending distally from the grip; a push rod configured to move within the cannula; a marker element configured for deployment using the push rod; and a plurality of articulators disposed within the cannula, wherein each articulator of the plurality of articulators is configured to move within the cannula to selectively bend a distal portion the cannula between a straight configuration and a bent configuration.

Example 22

The marker delivery device of Example 21, wherein each articulator of the plurality of articulators includes a rod with a distal end secured to a portion of the cannula.

Example 23

The marker delivery device of Example 21, wherein each articulator of the plurality of articulators includes a wire with a distal end secured to a portion of the cannula.

Example 24

The marker delivery device of any one or more of Examples 21 through 22, further comprising an actuator, wherein the actuator is configured to selectively apply tension to one or more articulators of the plurality of articulators.

Example 25

The marker delivery device of Example 24, further comprising a selector, wherein the selector is configured to manipulate the plurality of articulators or the actuator to selectively control which articulator of the plurality of articulators receives tension from the actuator.

Example 26

The marker delivery device of Example 25, wherein the selector is a thumbwheel positioned coaxially with the cannula.

Example 27

The marker delivery device of any one or more of Examples 21 through 26, wherein the cannula includes an open distal end, wherein each articulator of the plurality of articulators is configured to move within the cannula to selectively bend the distal portion the open distal end of the cannula between a loaded position and a deployment position.

Example 28

The marker delivery device of Example 27, wherein the marker element is configured for deployment through the open distal end of the cannula using the push rod.

Example 29

The marker delivery device of Example 28, wherein the cannula further includes a marker stop configured to releasably hold the marker element within the cannula.

Example 30

The marker delivery device of any one or more of Examples 21 through 26, wherein the push rod is configured to bend as the distal portion the cannula bends between the straight configuration and the bent configuration.

Example 31

A marker delivery device comprising: a grip; a cannula extending distally from the grip and defining a tissue inlet; an inner tube disposed within the cannula; and a push rod configured to move within the cannula, wherein the inner tube is configured to move relative to the cannula to induce a vacuum within the cannula to thereby draw tissue into the tissue inlet for marking using the push rod.

Example 32

The marker delivery device of Example 31, wherein the cannula defines an open distal end, wherein the tissue inlet is defined by the open distal end of the cannula.

Example 33

The marker delivery device of Example 31, wherein the cannula defines a side opening, wherein the tissue inlet is defined by the side opening of the cannula.

Example 34

The marker delivery device of any one or more of Examples 31 through 33, wherein the inner tube includes one or more seals configured to seal against an interior of the cannula.

Example 35

The marker delivery device of any one or more of Examples 31 through 34, wherein the push rod extends through the inner tube and is configured to move relative to the inner tube.

Example 36

The marker delivery device of Example 35, wherein inner tube includes a seal disposed between a portion of the inner tube and the push rod.

Example 37

The marker delivery device of any one or more of Examples 31 through 36, further comprising a lock, wherein the lock is configured to selectively secure the inner tube in a proximal position relative to the cannula.

Example 38

The marker delivery device of Example 37, wherein the lock is integral with the cannula.

Example 39

The marker delivery device of any one or more of Examples 31 through 38, further comprising a marker element, wherein the marker element is releasably secured to a distal end of the push rod.

Example 40

The marker delivery device of any one or more of Examples 31 through 38, further comprising a marker element, wherein the marker element is releasably secured to a distal end of the push rod, wherein the marker element includes one or more barbs configured to secure the marker element to tissue drawn into the tissue inlet.

Example 41

A method for marking a biopsy site, the method comprising: inserting a cannula of a marker delivery device into tissue; applying a marker material to a targeted region of tissue at the biopsy site through the cannula; and performing a biopsy procedure to extract a tissue sample from the targeted region after applying the maker material.

Example 42

The method of Example 41, wherein the step of applying the marker material includes injecting a marking fluid at the targeted region through the cannula.

Example 43

The method of any one or more of Examples 41 through 42, wherein the step of applying the marker material includes staining tissue associated with the targeted region.

Example 44

The method of any one or more of Examples 41 through 43, wherein the step of applying the marker material includes injecting a plurality of microspheres, nanospheres, or both at the targeted region through the cannula.

Example 45

The method of any one or more of Examples 41 through 44, wherein the cannula is fluidly coupled to a fluid source including a syringe, wherein the step of applying the marker material includes actuating the syringe.

Example 46

A marker for use in marking a biopsy site, the marker comprising: a body, a sharp tip on the distal end of the body, wherein the sharp tip is configured to pierce tissue, an arm extending proximally and outwardly relative to the sharp tip, wherein the arm defines an inwardly oriented barb disposed on a proximal end of the arm.

Example 47

The marker of Example 46, further comprising a base, wherein the base extends outwardly from the body.

Example 48

The marker of Example 47, wherein the base extends outwardly from the body at a length at least equivalent to the outward extension of the arm.

Example 49

A method for marking a biopsy site, the method comprising: inserting a cannula of a marker delivery device into tissue; inducing a vacuum within the cannula to pull at least some tissue into the cannula through a tissue port; advancing a marker within the cannula to drive the marker into the tissue pulled into the cannula; and releasing the vacuum induced within the cannula to release the tissue pulled into the cannula while the marker remains in the tissue.

Example 50

The method of Example 49, wherein the step of inducing a vacuum includes pulling a tube disposed within the cannula proximally relative to the cannula.

Example 51

A method for marking a biopsy site, the method comprising: inserting a cannula of a marker delivery device into a biopsy needle; articulating a distal portion of the cannula from a straight configuration to a curved configuration to position an open distal end of the cannula outside of the biopsy needle; and advancing a push rod disposed within the cannula to deploy a maker from the open distal end of the cannula.

Example 52

The method of Example 51, further comprising rotating a selector relative to the cannula to a desired clock position, wherein the step of articulating the distal portion of the cannula includes articulating the distal portion in a direction associated with the desired clock position.

V. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A marker delivery device comprising:
(a) a grip;
(b) a cannula extending distally from the grip;
(c) a push rod configured to move within the cannula and having distal end with one or more seals configured to seal against an interior of the cannula; and
(d) a marker element, the push rod being configured to generate a pressure within the cannula between the one or more seals and the marker element to eject the marker element from the cannula,
the marker element having one or more barbs, an elongate body, and including a base projecting from the elongate body in a circular disk configuration, the base being configured to seal against the interior of the cannula, the elongate body extending proximally from the one or more barbs, through and beyond the base.

2. The marker delivery device of claim 1, the cannula including an open distal end configured to permit the marker element to exit therethrough.

3. The marker delivery device of claim 1, the cannula including a side opening configured to permit the marker element to exit therethrough.

4. The marker delivery device of claim 1, the cannula including a marker stop configured to releasably engage the marker.

5. The marker delivery device of claim 1, the one or more seals including two seals.

6. The marker delivery device of claim 1, the one or more seals including one or more O-rings.

7. The marker delivery device of claim 1, the marker element further including a sharp tip and one or more arms extending proximally and outwardly relative to the sharp tip.

8. The marker delivery device of claim 7, each arm defining a barb of the one or more barbs.

9. The marker delivery device of claim 1, the marker element being disposed within a carrier.

10. The marker delivery device of claim 1, the outwardly projecting base being configured to balance the marker.

11. The marker delivery device of claim 1, the outwardly projecting base being configured to increase the propensity of the marker to remain in position once placed within tissue.

12. The marker delivery device of claim 1, the outwardly projecting base being configured to assist in building positive fluid pressure upon actuation of the push rod.

13. The marker delivery device of claim 1, the marker element being configured to obstruct the flow of fluid through the cannula between the marker element and the interior of the base.

14. The marker delivery device of claim 1, the grip extending in two directions outwardly relative to an axis defined by the cannula.

15. The marker delivery device of claim 1, wherein the one or more barbs of the marker element, the elongate body of the marker element, and the base of the marker element are all defined by the same material.

* * * * *